(12) United States Patent
Bogaert

(10) Patent No.: US 9,986,906 B2
(45) Date of Patent: Jun. 5, 2018

(54) WAVEFRONT GENERATION FOR OPHTHALMIC APPLICATIONS

(71) Applicant: AMO Groningen B.V., Groningen (NL)

(72) Inventor: Theophilus Bogaert, Groningen (NL)

(73) Assignee: AMO Groningen B.V., Groningen (NL)

( * ) Notice: Subject to any disclaimer, the term of this patent is extended or adjusted under 35 U.S.C. 154(b) by 22 days.

(21) Appl. No.: 15/354,962

(22) Filed: Nov. 17, 2016

(65) Prior Publication Data

US 2017/0065162 A1  Mar. 9, 2017

Related U.S. Application Data

(62) Division of application No. 14/202,738, filed on Mar. 10, 2014, now Pat. No. 9,510,748.

(60) Provisional application No. 61/792,347, filed on Mar. 15, 2013.

(51) Int. Cl.
| | | |
|---|---|---|
| A61B 3/00 | (2006.01) | |
| A61B 3/028 | (2006.01) | |
| A61B 3/10 | (2006.01) | |
| G02B 27/01 | (2006.01) | |
| A61F 9/008 | (2006.01) | |

(52) U.S. Cl.
CPC .......... *A61B 3/0025* (2013.01); *A61B 3/0041* (2013.01); *A61B 3/028* (2013.01); *A61B 3/1015* (2013.01); *G02B 27/017* (2013.01); *A61F 9/008* (2013.01); *A61F 2009/0088* (2013.01); *G02B 2027/011* (2013.01); *G02B 2027/014* (2013.01); *G02B 2027/0138* (2013.01); *G02B 2027/0178* (2013.01); *G02C 2202/10* (2013.01)

(58) Field of Classification Search
CPC ..... A61B 3/0025; A61B 3/0041; A61B 3/028; A61B 3/1015; G02B 27/017; A61F 9/008
USPC ........................................................ 351/246
See application file for complete search history.

(56) References Cited

U.S. PATENT DOCUMENTS

| | | |
|---|---|---|
| 2003/0071969 A1 | 4/2003 | Levine et al. |
| 2004/0100619 A1 | 5/2004 | Olivier et al. |

FOREIGN PATENT DOCUMENTS

| | | |
|---|---|---|
| WO | 0225347 A2 | 3/2002 |
| WO | 2013130670 A1 | 9/2013 |

OTHER PUBLICATIONS

International Search Report and Written Opinion for Application No. PCT/IB2014/000982, dated Sep. 19, 2014, 17 pages.

*Primary Examiner* — Jack Dinh
(74) *Attorney, Agent, or Firm* — Johnson & Johnson Surgical Vision, Inc.

(57) ABSTRACT

Embodiments of this invention relate to the generation of wavefronts for measurements, diagnostics, and treatment planning for ophthalmic applications. In some embodiments, a wavefront generator generates light having a uniform wavefront, which is focusable on the retina of an emmetropic eye by the normal function of the emmetropic eye. In some embodiments, the wavefront generator can generate light having a custom wavefront which is not focusable on the retina of the emmetropic eye. In some embodiments, the wavefront generator can receive information relating to an optical aberration of the eye, generate a custom wavefront, and project light having this custom wavefront, which in combination with the optical aberration of the eye is focusable on the retina.

21 Claims, 17 Drawing Sheets

WAVEFRONT GENERATION FOR OPHTHALMIC APPLICATIONS

CROSS-REFERENCES TO RELATED APPLICATIONS

This application is a divisional application under 35 USC § 120 of U.S. patent application Ser. No. 14/202,738, filed Mar. 10, 2014, now pending, which claims priority to U.S. provisional application No. 61/792,347 filed on Mar. 15, 2013. The entire contents of the two applications referenced above are incorporated herein by reference.

TECHNICAL FIELD

Embodiments of this invention generally relate to diagnosis and treatment of ophthalmic conditions, and more particularly to the generation of wavefronts for measurements, diagnostics, and treatment planning for ophthalmic applications.

SUMMARY OF THE INVENTION

Embodiments regarding the generation of wavefronts for measurements, diagnostics, and treatment planning for ophthalmic applications are disclosed. Exemplary areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

The present disclosure is described in conjunction with the appended figures.

In the appended figures, similar components and/or features may have the same reference label. Where the reference label is used in the specification, the description is applicable to any one of the similar components having the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION OF THE INVENTION

The ensuing description provides preferred exemplary embodiments) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

Wavefronts

A wavefront can be used to describe a wave including, for example, an electromagnetic wave. A wavefront is the locus of points having the same phase, and can be a line or curve in two dimensions, or surface of a wave that is propagating in three dimensions. Wavefront measurements can be used to evaluate the quality of an optical system and/or to identify imperfections in an optical system. In some embodiments, these measurements can be performed by a wavefront sensor which is a device that can measure wavefront aberration in a coherent signal. A Shack-Hartmann system is one embodiment of a wavefront sensor.

Figure 1:
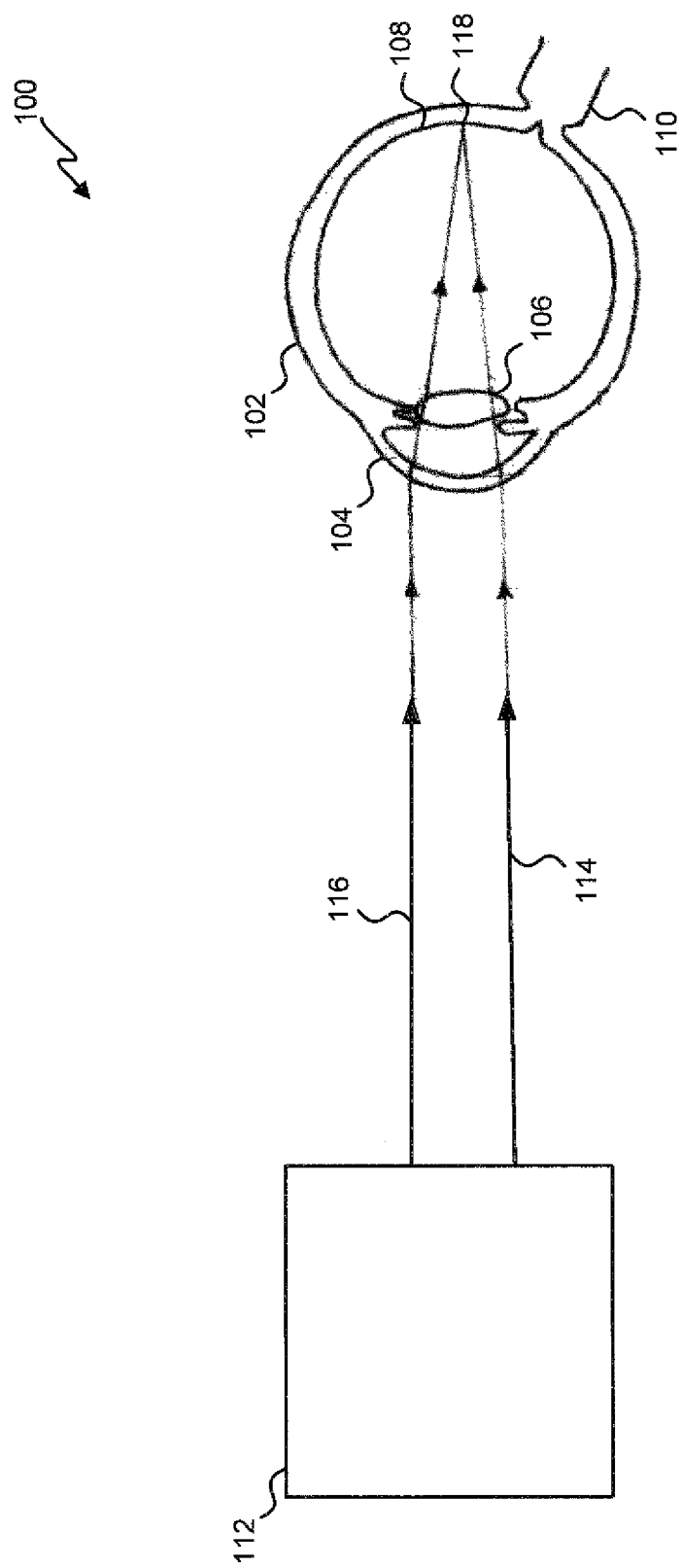
FIG. 1 is a schematic illustration of one embodiment of a visualization system.

With reference now to FIG. 1, a schematic illustration of one embodiment of a visualization system 100 is shown. The visualization system 100 includes an eye 102. The eye 102 can be any eye, and can be, for example, a human eye. The eye 102 includes the cornea 104, the lens 106, the retina 108, and the optic nerve 110.

The visualization system 100 further includes a wavefront generator 112. The wavefront generator 112 can include features configured to manipulate the wavefront of projected light. In some embodiments, the wavefront generator 112 can generate light having a uniform wavefront, which uniform wavefront is focusable on the retina 108 of an emmetropic eye by the normal function of the emmetropic eye. In some embodiments, the wavefront generator 112 can generate light having a custom wavefront, which light having a custom wavefront is not focusable on the retina 108 of the emmetropic eye by the normal function of the emmetropic eye.

In some embodiments, the wavefront generator 112 can receive information relating to an optical aberration of the eye 102, generate a custom wavefront, and can project light having this custom wavefront, which light having a custom wavefront in combination with the optical aberration of the eye 102 is focusable on the retina 108 of the eye 102.

In one embodiment, the wavefront generator can project light rays, and can specifically project a plurality of light rays including a first light ray 114 and a second light ray 116. As seen in FIG. 1, the light rays 114, 116 pass through the cornea 104 and the lens 106 and focus on the retina 108 of the eye 102. In some embodiments, the properties of the light rays 114, 116, including the strength and direction of the light rays 114, 116 can be affected by the wavefront generator 112, which effect can allow the light rays 114, 116 to focus on the retina 108 when the generated wavefront corresponds to the optical aberration of the eye 102.

Figure 1A:
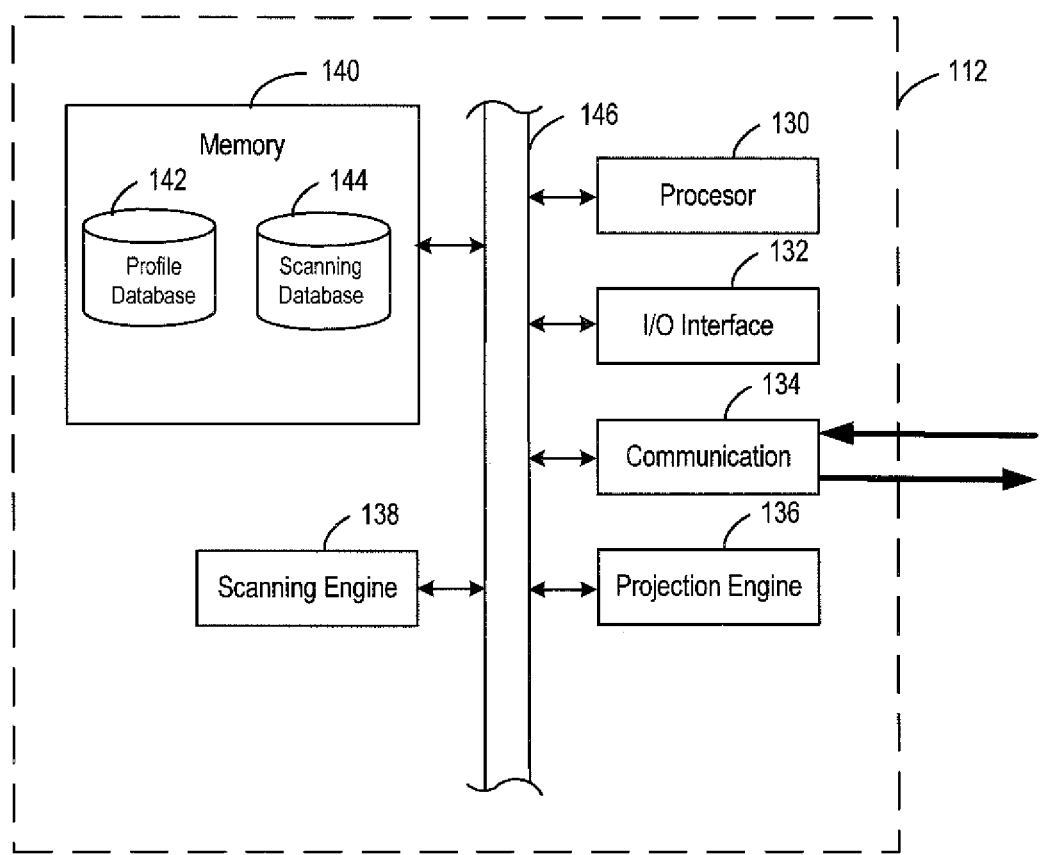
FIG. 1A is a schematic illustration of one embodiment of a wavefront generator.

With reference now to FIG. 1A, a schematic illustration of one embodiment of the wavefront generator 112 is shown. The wavefront generator 112 includes a processor 130. The processor 130 can provide instructions to, and receive information from the other components of the wavefront generator 112. The processor 130 can act according to stored instructions to control the other components of the wavefront generator 112. The processor 130 can comprise a microprocessor, such as a microprocessor from Intel® or Advanced Micro Devices, Inc.®, or the like.

The wavefront generator 112 can include an input/output interface 132. The input/output interface 132 communicates information, including outputs, to, and receives inputs from a user. The input/output interface 132 can include a screen, a speaker, a monitor, a keyboard, a microphone, a mouse, a touchpad, a keypad, or any other feature or features that can receive inputs from a user and provide information to a user.

The wavefront generator 112 can include a communication engine 134. The communication engine 134 can allow the wavefront generator 112 to communicatingly connect with other devices, and can allow the wavefront generator 112 to send and receive information from other devices. The communication engine 134 can include features configured to send and receive information, including, for example, an antenna, a modem, a transmitter, receiver, or any other feature that can send and receive information. The communication engine 134 can communicate via telephone, cable, fiber-optic, or any other wired communication network. In some embodiments, the communication engine 134 can communicate via cellular networks, WLAN networks, or any other wireless network.

The wavefront generator 112 includes a projection engine 136. The projection engine 136 can project light having a wavefront that is configured to allow the projected light focus on the retina 108 of the eye 102. The projection engine 136 can include features that can project light rays and can manipulate the wavefront of the projected light rays. In some embodiments, the projection engine 136 can include a wavefront display. The wavefront display can comprise any device capable of projecting one or several light rays and manipulating and/or controlling the wavefront of the one or several light rays. In some embodiments, the wavefront display can comprise, for example, a light source. The light source can comprise any controllable light generating device. In some embodiments, the wavefront display can comprise a matrix of individually controllable light sources. In one embodiment, for example, this matrix of individually controllable light sources can comprise a matrix of individually and independently controllable pixels. In some embodiments, the light source can be configured to project monochromatic light, and in some embodiments, the light source can be configured to project multiple colors of light. In some embodiments, for example, these colors can comprise the colors of any additive color model including, for example, an RGB model with the colors red, green, and blue. Advantageously, in some embodiments, different wavefront's can be generated for different colors so as to allow the correction for chromatic aberration.

The wavefront display can further include features configured to allow the controlled manipulation of the wavefront of the light rays generated by the light source. In one embodiment, for example, these features can comprise an array of lenslets, mirrors, or any other light reflecting or refracting feature that allows manipulation of the wavefront of light generated by the light source. In some embodiments, for example, the lenslets in the lenslet array can comprise fresnel lenses. In one specific embodiment, the display can comprise a Shack-Hartmann system, and specifically, a reverse Shack-Hartmann system.

The wavefront generator 112 includes a scanning engine 138. In some embodiments, for example, the scanning engine 138 can be configured to capture a wavefront shape of light that has passed through the user's eye 102, and based on the wavefront shape, calculate the optical aberration of the eye 102. In some embodiments, the scanning engine 138 can be configured to determine information relating to the position of the user's eye relative to the wavefront generator 112. In some embodiments, for example, this can include determining the distance between the wavefront generator 112 and the user's eye 102 and/or the angle between the wavefront generator 112 and the user's eye 102.

The scanning engine 138 can include features configured to determine the optical aberration of the user's eye 102. In some embodiments these features can perform wavefront analysis on the eye 102, and these features can specifically include a wavefront sensor. In one embodiment, the wavefront sensor can be an optical capture device which can be any device including light sensing components and can be, for example, a camera and/or scanner. The wavefront sensor can comprise a plurality of photoreceptors which can be, for example, arranged into a matrix of photoreceptors. The wavefront sensor can further comprise an array of lenslets, mirrors, and/or any other features capable of reflecting and/or refracting light. In one embodiment, each lenslet and/or mirror can be associated with the subset of photoreceptors from the matrix of photoreceptors. In some embodiments, for example, this subset of photoreceptors associated with each lenslet and/or mirror is constant, and in some embodiments, this subset of photoreceptors associated with each lenslet and/or mirror can dynamic. In some embodiments, this association can be determined by the lenslet through which light impinging on one or several photoreceptors passes. In some embodiments, the number of photoreceptors associated with each lenslet can vary based on the size of the lenslet, the distance between the lenslet and the photoreceptor array, and the size of the photoreceptors and/or the resolution of the photoreceptor matrix. The number of photoreceptors associated with each lenslet can comprise 1, 2, 3, 4, 5, 6, 7, 8, 9, 10, 20, 50, 100, and/or any other or intermediate number of photoreceptors. In one embodiment, for example, the wavefront sensor can comprise a Shack-Hartmann system.

The scanning engine 138 can include features configured to determine information relating to the position of the user's eye relative to the wavefront generator 112. In some embodiments, for example, these features can include a sensor such as, for example, an infrared sensor configured to detect the eye 102, the distance from the wavefront generator 112 to the eye 102, and the angle of the wavefront generator 112 relative to the eye 102, and in some embodiments, relative to the pupil of the eye.

In some embodiments, the scanning engine 138 can determine information relating to the position of the user's eye relative to the wavefront generator 112 by generating an image of the user's eye. In some embodiments, a parameter of the image of the user's eye can be measured and compared to a standard and/or stored parameter of the user's eye. In one embodiment, for example, this parameter can be the diameter of the iris, including, for example, the horizontal diameter of the iris, the distance between the pupils of the user's eyes, or the horizontal diameter of the eye.

The wavefront generator 112 can include memory 140. The memory 140 can include stored instructions that, when executed by the processor 130, control the operation of the wavefront generator 112. The details of the memory 140 are discussed at greater length below.

As seen in FIG. 1A, the memory can include one or several databases including, for example, a profile database 142 and a scanning database 144.

The profile database 142 can include information relating to a user. This information can include, for example, information identifying the user, information identifying the optical aberration in one or both of the user's eyes, information identifying the custom wavefront generated for the user, and/or any other desired information. In some embodiments, the information in the profile database 142 can be provided by the user, and in some embodiments, the information in the profile database 142 can be generated by components of the wavefront generator 112. Thus, for example, in some embodiments the information in the profile database can be received by the input/output interface 132 from the user, can be received from other devices by the communication engine 134, can be calculated by the processor 130, and/or can be gathered by the scanning engine 138.

The scanning database 144 can include data relating to optical aberrations detected by the scanning engine 138. In some embodiments, for example, a user of the wavefront generator 112 may not be associated with a profile stored within the profile database 144. In such an embodiment, for example, data relating to an optical aberration generated by the scanning engine 138 can be stored within the scanning database 144. In some embodiments, this information can be used until the user requests the generation of new optical aberration data, at which point the new optical aberration data can be added to the scanning database 144 and can replace the old optical aberration data stored in the scanning database 144, or can be additionally stored with the old optical aberration data.

Figure 2:
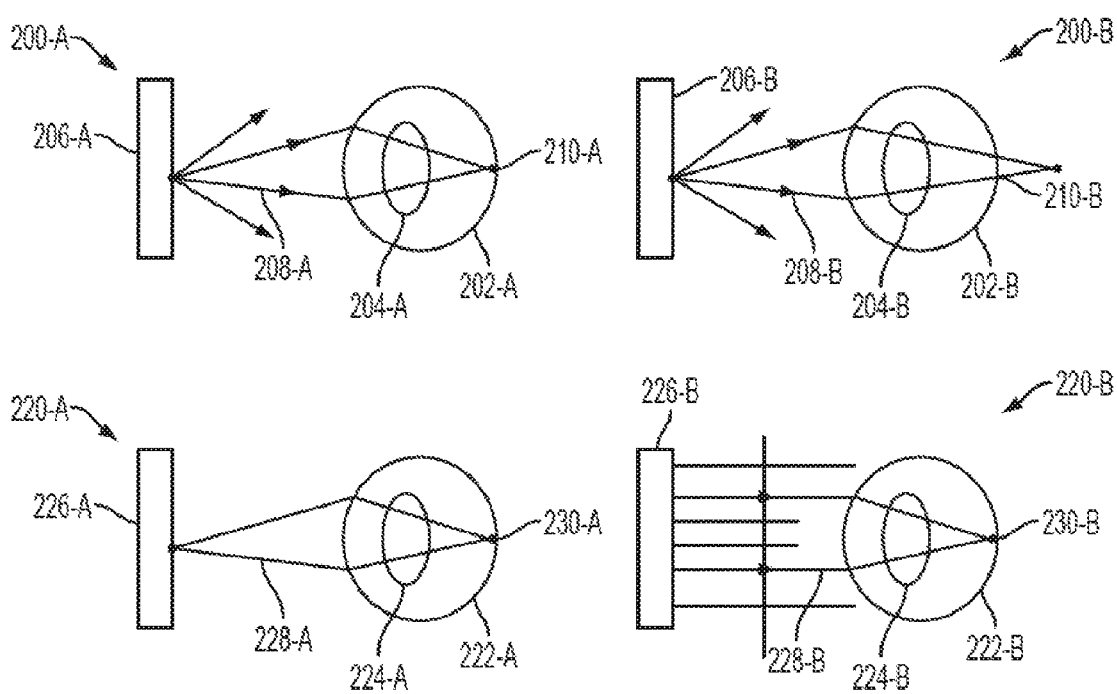
FIG. 2 is a schematic illustration of the interaction of eyes with both a traditional display and a custom wavefront generating display.

With reference now to FIG. 2, a schematic illustration of the interaction of eyes with both a traditional display and a custom wavefront generating display is shown. FIG. 2 depicts a first instance 200-A having an emmetropic eye 202-A having a lens 204-A. The first instance 200-A further depicts a traditional display 206-A that is generating a plurality of light rays including light rays 208-A which enter into the eye 202-A. As seen in the first instance 200-A, the light rays 208-A enter the eye 202-A and are focused by the cornea and the lens 204-A onto the retina 210-A.

FIG. 2 depicts a second instance 200-B having a non-emmetropic eye 202-B with a lens 204-B. The second instance 200-B further depicts a traditional display 206-B that is generating a plurality of light rays, including light rays 208-B which enter into the eye 202-B. As seen in the second instance 200-B, the light rays 208-B enter the eye 202-B and are focused by the cornea and the lens 204-B, but do not focus on the retina 210-B, but rather, come to a focus behind the retina 210-B.

As is apparent in comparing the first instance 200-A with the second instance 200-B, the plurality of light rays generated by the traditional display 206-A, 206-B are the same for both the emmetropic eye 202-A and the non-emmetropic eye 202-B.

FIG. 2 depicts a third instance 220-A having a emmetropic eye 222-A with a lens 224-A. The third instance 220-A further depicts a wavefront display 226-A that is generating a plurality of light rays, including light rays 228-A which enter into emmetropic eye 222-A. As seen in the third instance 220-A, the light rays enter the eye 222-A and are focused by the cornea and lens 224-A onto the retina 230-A.

FIG. 2 depicts a fourth instance 220-B having a non-emmetropic eye 222-B with a lens 224-B. The fourth instance 220-B further depicts a wavefront display 226-B that is generating a plurality of light rays, including light rays 228-B which enter into eye 222-B. As seen in the fourth instance 220-B, the light rays 228-B enter the eye 222-B and are focused by the cornea and lens 224-B onto the retina 230-B.

As is apparent in comparing the third instance 220-A with the fourth instance 220-B, the plurality of light rays generated by the wavefront display 226-A for the emmetropic eye 222-A are different from the plurality of light rays generated by the wavefront display 226-B for the non-emmetropic eye 222-B. As discussed above, in some embodiments, the wavefront display 226-A, 226-B can generate a custom wavefront that matches the optical aberration of the user's eye such that when the light having the custom wavefront passes through the eye having the corresponding optical aberration, the light focuses on the retina.

Figure 3A:
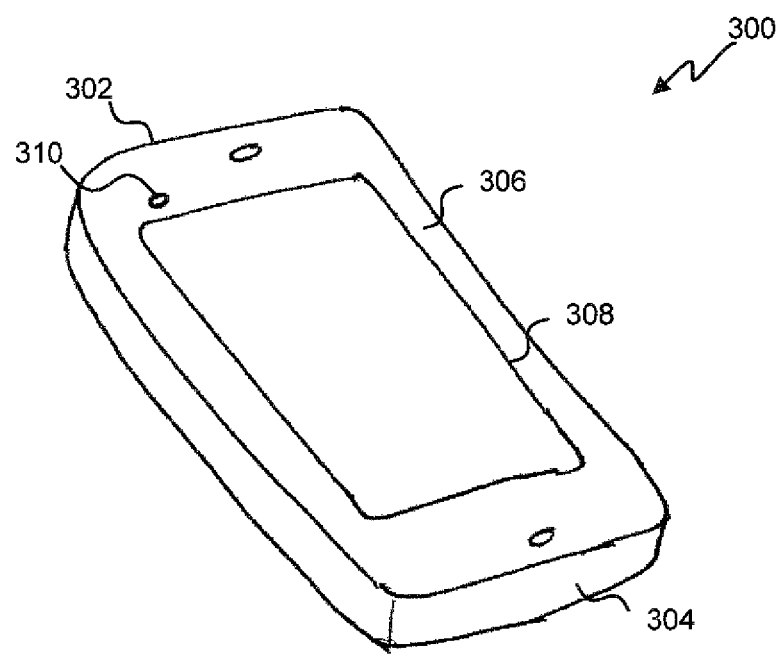
FIGS. 3A and 3B are perspective views of one embodiment of a wavefront generator incorporated into a handheld electronic device.

With reference now to FIG. 3A, a perspective view of one embodiment of a handheld electronic device 300 incorporating the wavefront generator 112 is shown. The handheld electronic device 300 can be any mobile device. In some embodiments, the handheld electronic device 300 can comprise a cell phone, a tablet, a laptop, a navigation system, smart phone, or any other desired mobile device. In some embodiments, the handheld electronic device 300 can include a top 302, a bottom 304, and the front 306. In some embodiments, the front of the handheld electronic device 300 can include a display 308 which can include, for example, a wave front display. In some embodiments, the display 308 can be a component of the earlier discussed projection engine 136.

The handheld electronic device 300 can, in some embodiments, further include a ranging sensor 310. In some embodiments, the ranging sensor 310 can comprise an infrared sensor, and can be configured to measure and/or ascertain the distance between the user's eye and the wavefront display 308 of the handheld electronic device 300, and/or in some embodiments, the ranging sensor 310 can be configured to measure and/or ascertain the angle between the user's eye and the wavefront display 308 of the handheld electronic device 300.

Figure 3B:
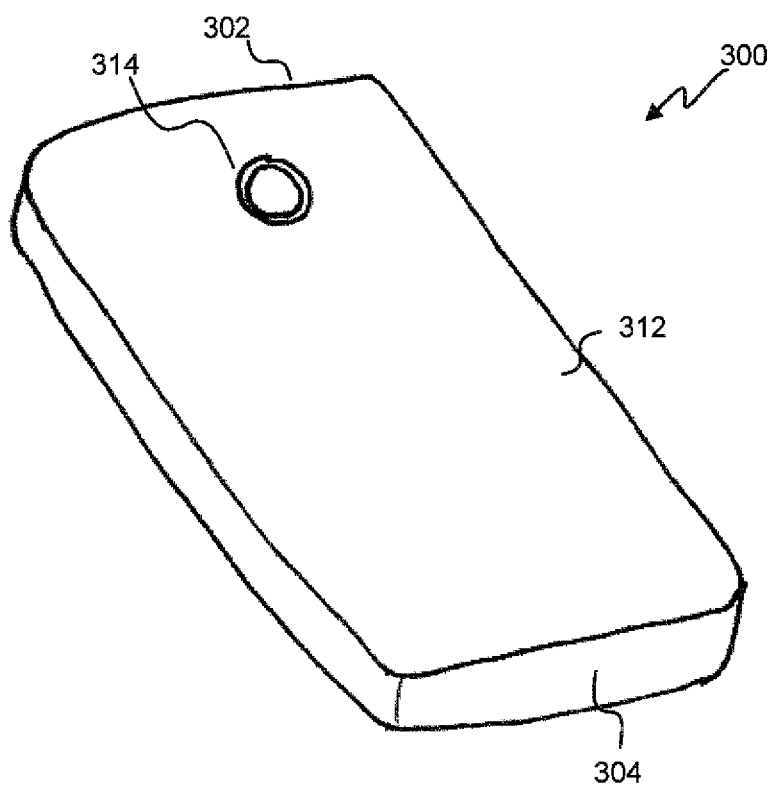

With reference now to FIG. 3B, a perspective view of the handheld electronic device 300 is shown. As seen in FIG. 3B, the handheld electronic device includes the top 302, the bottom 304, and the back 312. In some embodiments, for example, the back 312 of the handheld electronic device can include an optical capture device 314 which can be any device including light sensing components and can be, for example, a camera and/or scanner. The optical capture device 314 can be a component of the scanning engine 138, and can include a wavefront sensor. In some embodiments, for example, the optical capture device 314 can be configured to measure and/or analyze a wavefront as it passes, and/or after it passes through the eye 102 to thereby measure any optical aberration existing in the eye 102. In some embodiments, for example, the wavefront sensor can include a Shack-Hartmann system. In some embodiments, the optical capture device 314 can include a sensor configured to detect the position of the eye 102 relative to the handheld electronic device 300.

Figure 4:
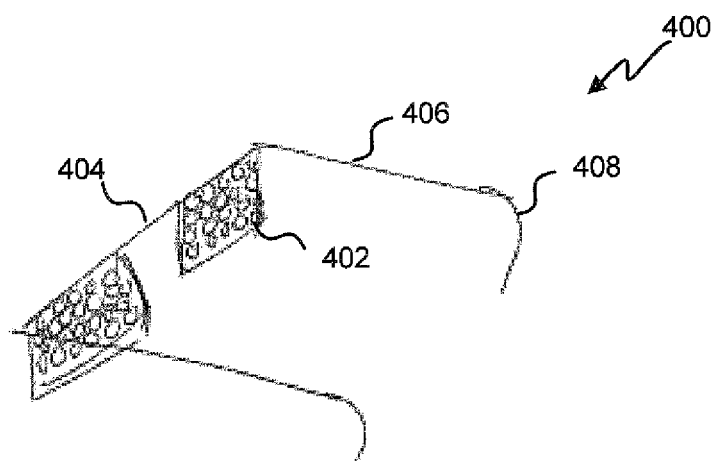
FIG. 4 is a perspective view of one embodiment of a wavefront generator incorporated into a pair of glasses.

With reference now to FIG. 4, a perspective view of one embodiment of a wavefront generator 112 incorporated into a pair of glasses 400 is shown. The glasses 400 include lenses 402, which lenses 402 are connected with the wavefront generator 112. The lenses 402 are connected by a bridge 400 for, and connect, via two temples 406, to earpieces 408. In some embodiments, the lenses 402 can be substantially planar lenses as depicted in FIG. 4, and in some embodiments, the lenses 402 can comprise curved lenses 42. In some embodiments, the lenses 402 can be curved so as to wrap around the users eye and allow imaging onto a larger portion of the retina. In some embodiments, these curved lenses 402 can be created using, for example, a flexible display and by situating the lenslet array on a curved surface. In some embodiments, the distance between the curved lenslet array and the curved light source surface can be, for example, 1× the focal length of the lenslet forming the lenslet array.

Figure 5:
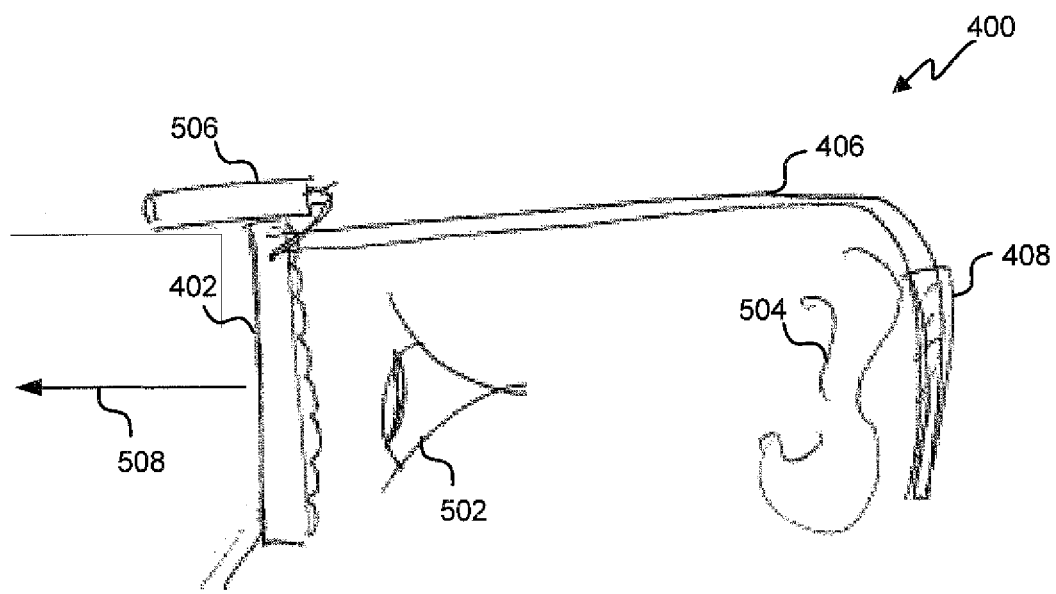
FIG. 5 is a side view of one embodiment of wavefront generator incorporated into a pair of glasses.

A side view of the glasses 400 is shown in FIG. 5. As seen in FIG. 5, the lens 402 of the glasses 400 can be positioned directly in front of, and in the line of sight of an eye 502. In this configuration, light generated by the wavefront generator 112 connected to the lens 402 can pass to the eye 502 and focus on the retina of the eye 502. As also seen in FIG. 5, the glasses 400 can be held in place in front of the eye via the earpiece 408 which can be positioned behind the ear 504 of the user.

In some embodiments, the wavefront generator 112 can cover all of the field of view of the eye, or a portion of the field of view of the. In some embodiments, for example, the wavefront generator 112 can be located in a peripheral region of the user's field of view. This can advantageously need the central vision of the user unrestricted while allowing the wavefront generator 112 to provide images to the user that augment the objects that the user is viewing. In some embodiments, this augmentation can include increasing the contrast of perceived images, recognizing the contours of images and adding these contours to the real image on the retina, and/or retrieving any other information relating to the real image and providing that to the retina. In some embodiments, for example, the wavefront generator can be located in a peripheral portion of one or both of the lenses 402 of the glasses 400.

In some embodiments, the wavefront generator 112 can be configured to allow near vision as well as far vision. In some embodiments, for example, the wavefront generator 112 can be configured to determine the viewing distance and to adjust the wavefront accordingly, and in some embodiments the wavefront generator 112 can be configured to receive an input from the user identifying the desired viewing distance. In some embodiments, for example, glasses 400 including such wavefront generator 112 can be used to replace traditional corrective optics such as, for example reading glasses and/or bifocals.

As seen in FIG. 5, in some embodiments, the glasses 400 can include a camera and/or magnifying device 506. In some embodiments, for example, the camera and/or magnifying device 506 can include features configured to gather image data in the direction perpendicular to the lenses, which direction is indicated in FIG. 5 by arrow 508. In some embodiments, for example, the image data collected by the camera and/or magnifying device 506 can be displayed via the wavefront generator 112 to the user. In some embodiments, for example, the user can control the level of magnification of the camera and/or magnifying device 506 to thereby provide the user with assumed in views of the gathered image data.

Figure 6:
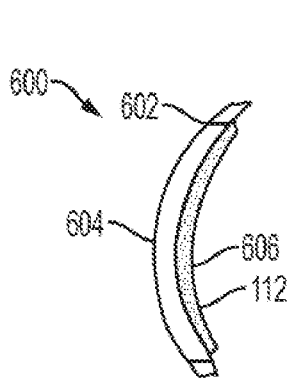
FIG. 6 is a side view of one embodiment of a wavefront generator incorporated into a contact lens.

With reference now to FIG. 6, a perspective view of one embodiment of a contact lens system 600 is shown, which contact lens system 600 can include, for example, an intraocular lens system. The contact lens system 600 can comprise a convex lens 602 having a front 604 and a back 606. In some embodiments, the convex lens 602 can house some or all of the components of the wavefront generator 112. In some embodiments, some or all of the components of the wavefront generator 112 can be embedded in the convex lens 602 between the front 604 and the back 606. In one specific embodiment, the back 606 of the convex lens 602 can comprise a protective coating over the components of the wavefront generator 112. This protective coating can be biocompatible to allow the convex lens 602 to be placed on an eye.

In some embodiments, for example, the contact lens system 600 can be configured so that the distance "x1" between the light source surface and the principal plane of the lenslet, and the distance "x2" between lenslet principal plane and the retina is governed by the following formula:

$$\frac{1}{x1} + \frac{1}{x2} = \frac{1}{f}$$

wherein "f" as the focal point resulting in sharp image forming on the retina.

Figure 7:
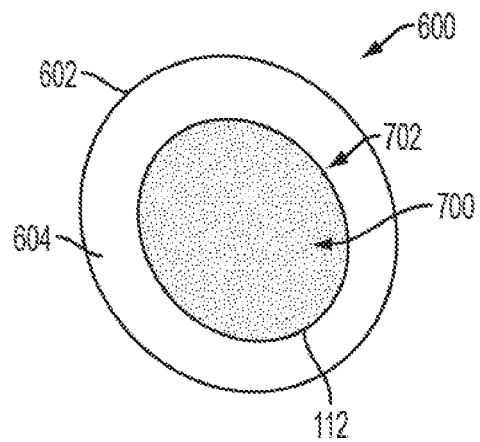
FIG. 7 is a front view of one embodiment of a wavefront generator incorporated into the contact lens.

With reference now to FIG. 7, a front view of one embodiment of the contact lens system 600 is shown. As seen in FIG. 7, the contact lens system 600 has a convex lens 602 with the front 604. As further seen in FIG. 7, in some embodiments, the convex lens 602 can comprise a central portion 700 and the boundary portion 702 radially surrounding the central portion 700 of the convex lens 602 when viewed from the front. In some embodiments, the different portions 700, 702 of the convex lens 602 can contain different components of the wavefront generator 112. In the embodiment depicted in FIG. 7, the central portion 700 of the convex lens 602 can include, for example, the projection engine 136 and/or the scanning engine 138, and the boundary portion 702 can include, for example, the processor 130, the communication engine 134, memory 140, an antenna, and components configured to power the wavefront generator 112 such as, for example, an antenna for receiving radio energy, a solar cell, inductive coils, or any other desired power source. Advantageously, the positioning of the scanning and projection engines 136, 138 in the central portion 700 of the convex lens 602 can facilitate positioning of those components in front of the pupil of the eye 102 which can increase the effectiveness of the contact lens system 600. Further, the placement of the components of the wavefront generator 112 in different portions 700, 702 of the convex lens 602 can allow the minimization of the distance between the front 604 and the back 606 of the convex lens 602, and thereby limit the thickness of the convex lens 602 and increase user comfort and using the contact lens system 600.

Figure 8:
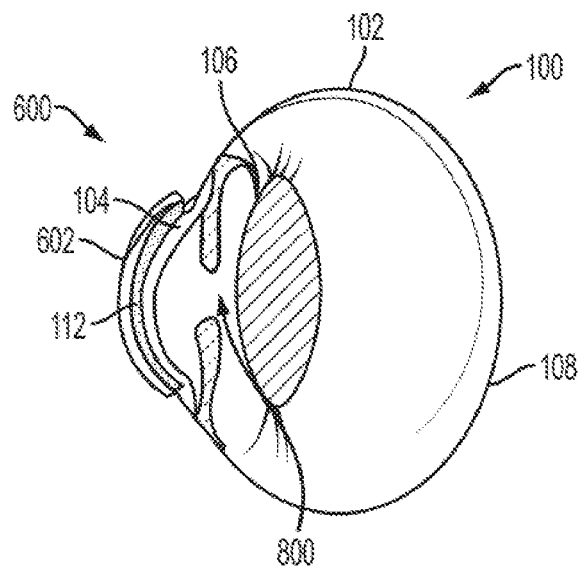
FIG. 8 is a side view of one embodiment of a contact lens incorporating a wavefront generator that is placed on an eye.

With reference now to FIG. 8, one embodiment of a visualization system 100 is shown. In this embodiment of the visualization system 100, the wavefront generator 112 is located within the convex lens 602 of the contact lens system 600. As further seen in FIG. 8, the contact lens system 600 is positioned on cornea 104 of the eye 102 so as to allow light rays generated by the wavefront generator 112 to pass through the pupil 800 of the eye 102 and impinge on the retina 108.

Figure 9:
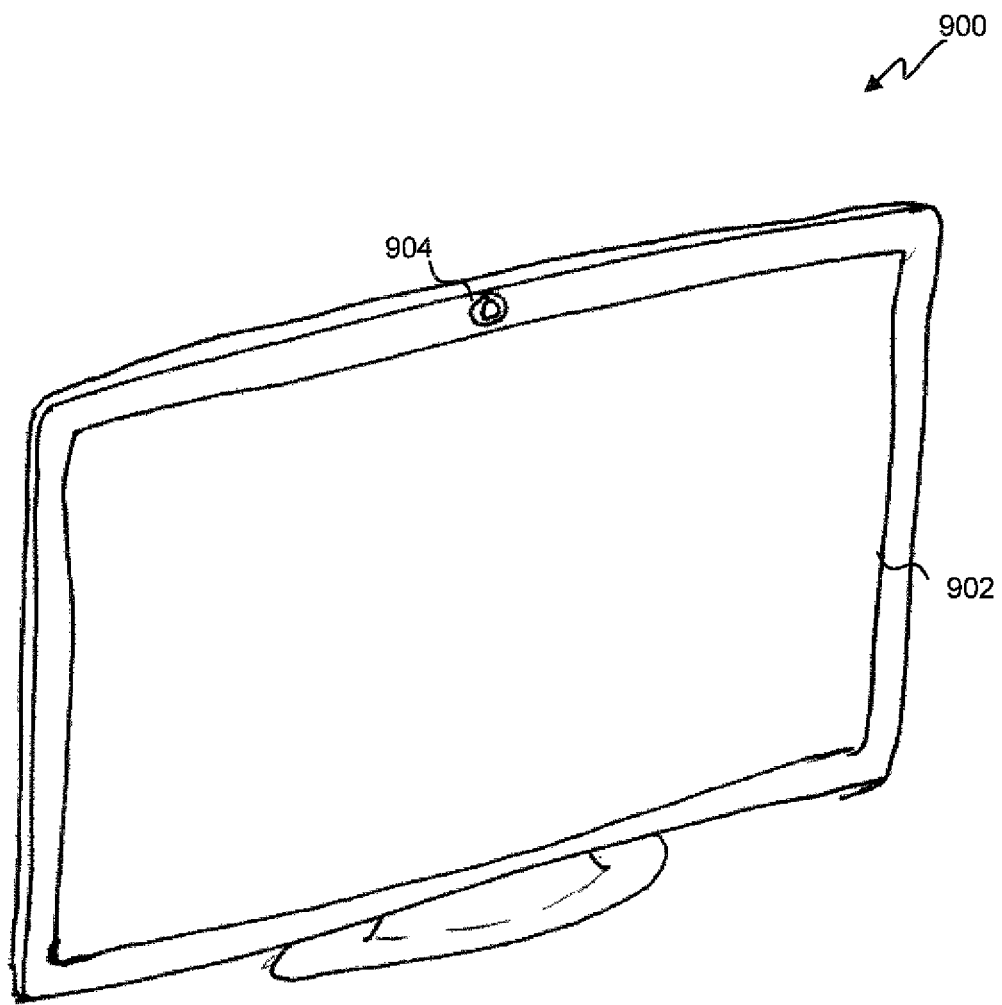
FIG. 9 is a perspective view of one embodiment of a wavefront generator incorporated into the display.

With reference now to FIG. 9, one embodiment of a display system 900 incorporating some or all of the components of the wavefront generator 112 is shown. The display system 900 can be used to view images and can comprise, for example, a television, a computer screen and/or monitor, or any non-held electronic device used to view images. The display system 900 can include a display 902 which can include, for example, a wavefront display. In some embodiments, the display 902 can be a component of the earlier discussed projection engine 136.

As further seen in FIG. 9, the display system 900 can include an optical capture device 904 which can be any device including light sensing components and can be, for example, a camera and/or scanner. The optical capture device 904 can be a component of the scanning engine 138, and can include a wavefront sensor. In some embodiments, for example, the optical capture device 904 can be configured to measure and/or analyze a wavefront as it and/or after it passes through the eye 102 to thereby measure any optical aberration existing in the eye 102. In some embodiments, for example, the wavefront sensor can include a Shack-Hartmann system.

Figure 10:
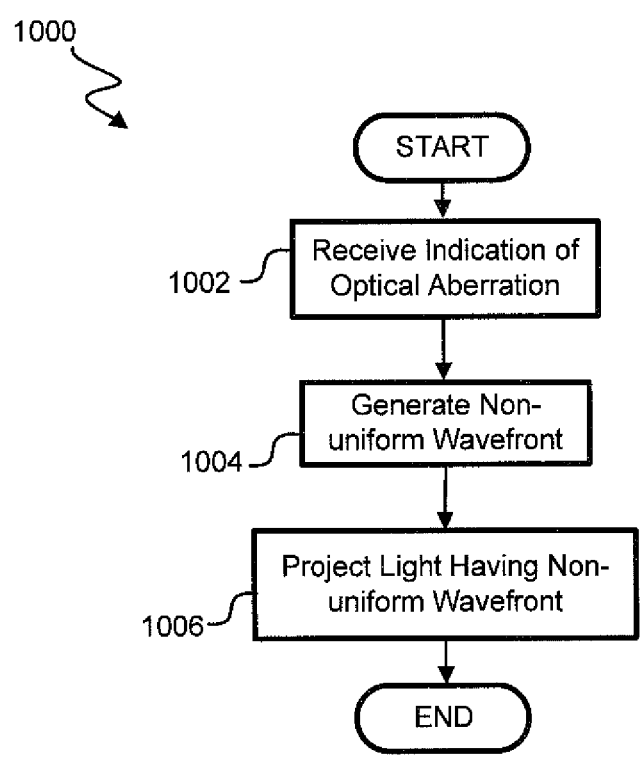
FIG. 10 is a flowchart illustrating one embodiment of a process for projecting light having a custom wavefront.

With reference now to FIG. 10, a flowchart illustrating one embodiment of a process 1000 for projecting light having a customized wavefront is shown. As discussed above, in some embodiments, this process 1000 can be used to generate light having a custom wavefront corresponding to the optical aberration of a user's eye. This correspondence between the custom wavefront and the optical aberration of the user's eye allows light having the custom wavefront to focus on the retina of the user's eye, and thereby allow the user to clearly see the projected light.

The process begins at block 1002 wherein an indication of the optical aberration is received. In some embodiments, the indication of the optical aberration can include optical aberration data that identifies the optical aberration of the user's eye. In some embodiments, for example, the indication the optical aberration can be received from a component of the wavefront generator 112 including, for example, the input/output interface 132, the communication engine 134, the scanning engine 138, and/or the memory including the profile database 142 and/or the scanning database 144. In some embodiments, components of the wavefront generator 112 can receive the indication of the optical aberration from a source outside of the wavefront generator 112 including, for example, from the user via the input/output interface 132, from a source of medical records such as, for example, from a medical service provider via the communication engine 134, or from any other source possessing optical aberration data for the user.

After the indication of the optical aberration is received, the process 1000 proceeds to block 1004 wherein the custom wavefront is generated. In the context of the present application, the custom wavefront includes the data describing a desired wavefront and can include, for example, dimensions. In some embodiments, the custom wavefront corresponds to the indication of the optical aberration in that light having the custom wavefront and passing through the eye with that optical aberration focuses on the retina of the eye. In some embodiments, for example, the custom wavefront can be generated by a component of the wavefront generator 112 including, for example, the processor 130 and/or the projection engine 136. In some embodiments, for example, the custom wavefront can be retrieved from a component of the wavefront generator 112 including the input/output interface 132, the communication engine 134, and/or the memory 140 including the profile database 142 and/or the scanning database 144. In some embodiments, for example, the custom wavefront can be received input into the input/output interface 132 by the user and/or the custom wavefront can be received from another source including, for example, a computer configured to generate and/or store the custom wavefront via the communication engine 134.

After the custom waveform is generated, the process 1000 proceeds to block 1006 wherein light having the custom wavefront is projected. In some embodiments, for example, the projecting of light having the custom wavefront comprises manipulating the wavefront of the light so that the wavefront of the light matches the generated custom wavefront. In some embodiments, this can be performed by the projection engine 136 and/or a component of the projection engine 136 such as the wavefront display.

In some embodiments, for example, the projected light having a nonuniform wavefront can comprise data that is imaged on the retina. This image data can comprise an image that can, in some embodiments, include one or several text strings, video images, or any other desired image. In some embodiments, this image data can comprise a raster image created from a plurality of pixels and/or dots. In embodiments in which the image data comprises a raster image, a generator 112 can image each of the pixels and/or dots onto a region of the retina. The imaging of each of the pixels and/or dots onto a region of the retina can be controlled so that the aggregate of imaged tunes and/or dots forms the image on the retina. In embodiments in which video images are imaged on the retina, each of the pixels and/or thoughts that are imaged onto the retina can be refreshed as they change. In some embodiments, for example, the video images can be generated by a camera, and in some embodiments, the video images can be linked to virtual reality system. Advantageously, in some embodiments in which the video images are generated by a camera associated with the wavefront generator 112, the wavefront generator 112 can allow the user to see images generated by light in the nonvisible spectrum. This can be achieved when the camera associated with the wavefront generator 112 detects nonvisible light, and then converts that nonvisible light visible light which is imaged by the projection engine 136. In some embodiments, this can advantageously allow the user to see infrared light, and can thereby provide a night vision capability.

In some embodiments, the image can be projected onto all of the retina or a portion of the retina. In some embodiments, for example, the image can fill of patient's and/or user's field of view, and/or a portion of a patient's and/or user's field of view including, for example, approximately 20 percent of the patient's and/or user's field of view, approximately 30 percent of the patient's and/or user's field of view, approximately 50 percent of the patient's and/or user's field of view, approximately 75 percent of the patient's and/or user's field of view, approximately 90 percent of the patient's and/or user's field of view, and/or any other or intermediate percent of the patient's and/or user's field of view.

Figure 10A:
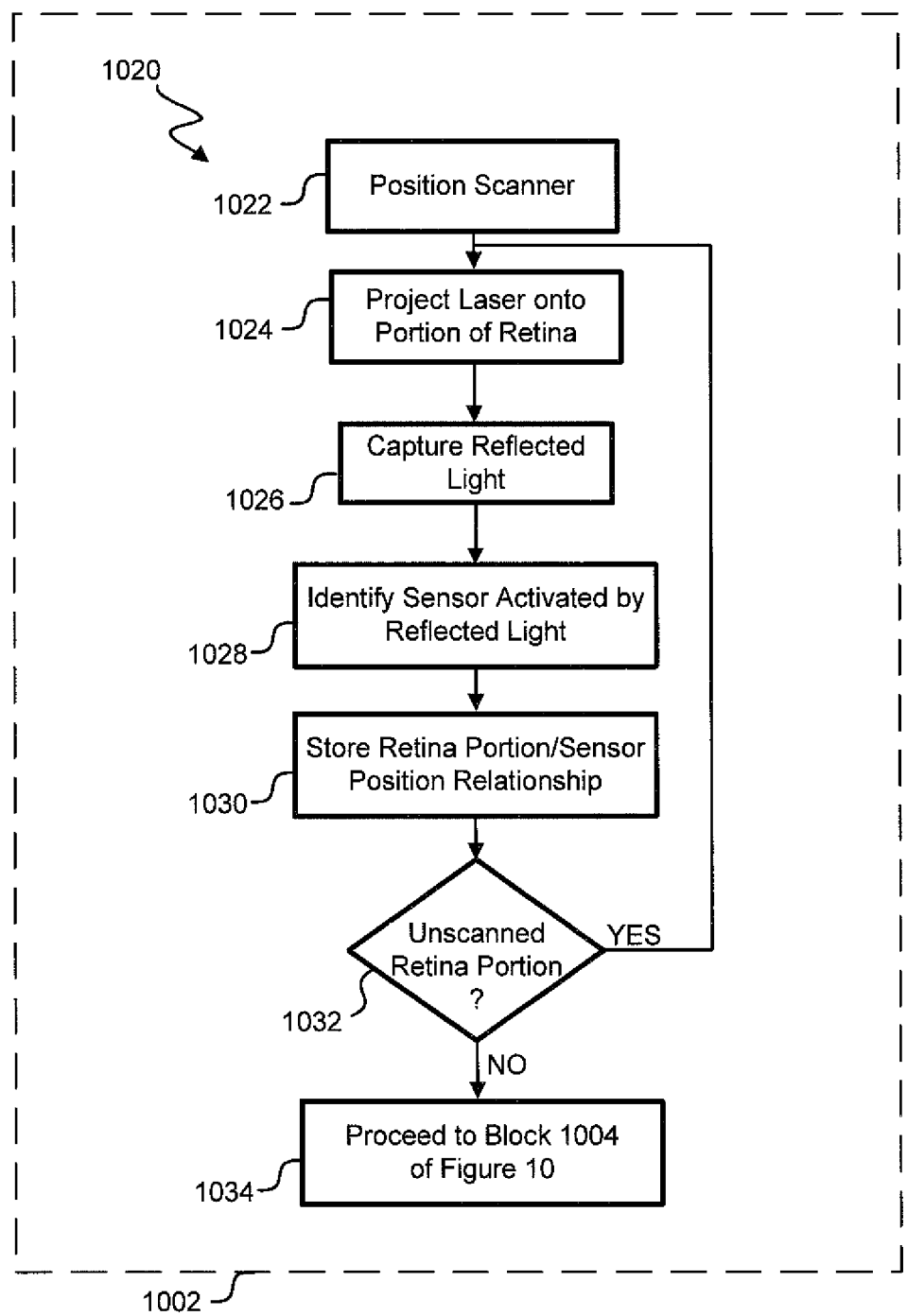
FIG. 10A is a flowchart illustrating one embodiment of a process for receiving an indication of an optical aberration.

With reference now to FIG. 10A, a flowchart illustrating a process 1020 for receiving an indication of an optical aberration is shown. In some embodiments, the process 1020 can be performed as a sub-process of block 1002 of FIG. 10. Process 1020 can be performed by the wavefront generator 112 and/or by one or several components of the wavefront generator 112 including, for example, the processor 130.

The process 1020 begins, in block 1022 wherein the scanner is positioned. In some embodiments, a scanner can comprise a component of the scanning engine 138 and specifically a component of the wavefront sensor of the scanning engine 138. In some embodiments, for example, the scanner can be positioned in front of one or both of the user's eyes 102, and in some embodiments, the scanner may be temporarily mounted to the user's head such as when the scanners are incorporated into a pair of glasses and/or into a headpiece.

After the scanner has been position, the process 1020 proceeds to block 1024 wherein a coherent beam of light is projected onto the retina of the user's eye. In some embodiments, the coherent beam of light can be configured so as not to temporarily and/or permanently damage the retina, but rather to reflect a portion of the coherent beam of light to allow the evaluation of the optical aberration of the eye. In some embodiments, for example, the coherent beam of light can comprise a laser.

In one embodiment, for example, in which the scanner comprises a matrix of photoreceptors and/or sensors, the laser can be projected from a center point of the matrix of photoreceptors and/or sensors. In some embodiments, for example, the laser can be projected from the center of a subset of the photoreceptors and/or sensors such as, for example, from the center the subset of photoreceptors and/or sensors associated with a single lenslet and/or mirror.

After the coherent beam of light is projected onto a portion of the retina, the process 1020 proceeds to block 1026 wherein the light reflected back off the retina is captured by one or several of the photoreceptors and/or sensors in the matrix of photoreceptors and/or sensors. After the reflected light is captured, the process 1020 proceeds to block 1028 wherein the one or several photoreceptors and/or sensors activated by the reflected light are identified. In some embodiments, for example, this can include identifying the position within the matrix of photoreceptors and/or sensors of the activated photoreceptors and/or sensors. In some embodiments, for example, this identification can be made according to the column/row position of each of the photoreceptors and/or sensors that are activated by the reflected light in the matrix of photoreceptors and/or sensors, and in some embodiments, for example, this identification can be made according to the column/row position of the lenslet and/or mirror having an associated and activated photoreceptors and/or sensor, and an identifier of the position of the activated photoreceptor and/or sensor within the group of photoreceptors and/or sensors associated with the lenslet and/or mirror.

After the photoreceptor and/or sensor activated by the reflected light is identified, the process 1020 proceeds to block 1030 wherein the location of the portion of the retina onto which the coherent beam of light was shown is identified and stored in association with the location of the photoreceptors and/or sensors that were activated by the reflection of the coherent beam of light off of that portion of the retina. In some embodiments, this can include storing the relationship between the retina portion illuminated by the coherent beam of light in the sensor position of sensors activated by the reflection of that coherent beam of light.

After the retina portion/sensor position relationship has been stored, the process 1020 proceeds to decision state and 32 wherein it is determined if there are any remaining un-scanned portions of the retina. In some embodiments, for example, this can include determining whether the above recited steps have been performed for portions covering the entire area of the retina. If it is determined that there is an un-scanned retina portion, the process 1020 returns to block 1024 wherein the coherent beam of light is projected onto an un-scanned portion of the retina. If it is determined at decision state 1032 that there are no un-scanned retina portions, then the process 1020 proceeds to block 1034 and returns to block 1004 of FIG. 10.

Figure 10B:
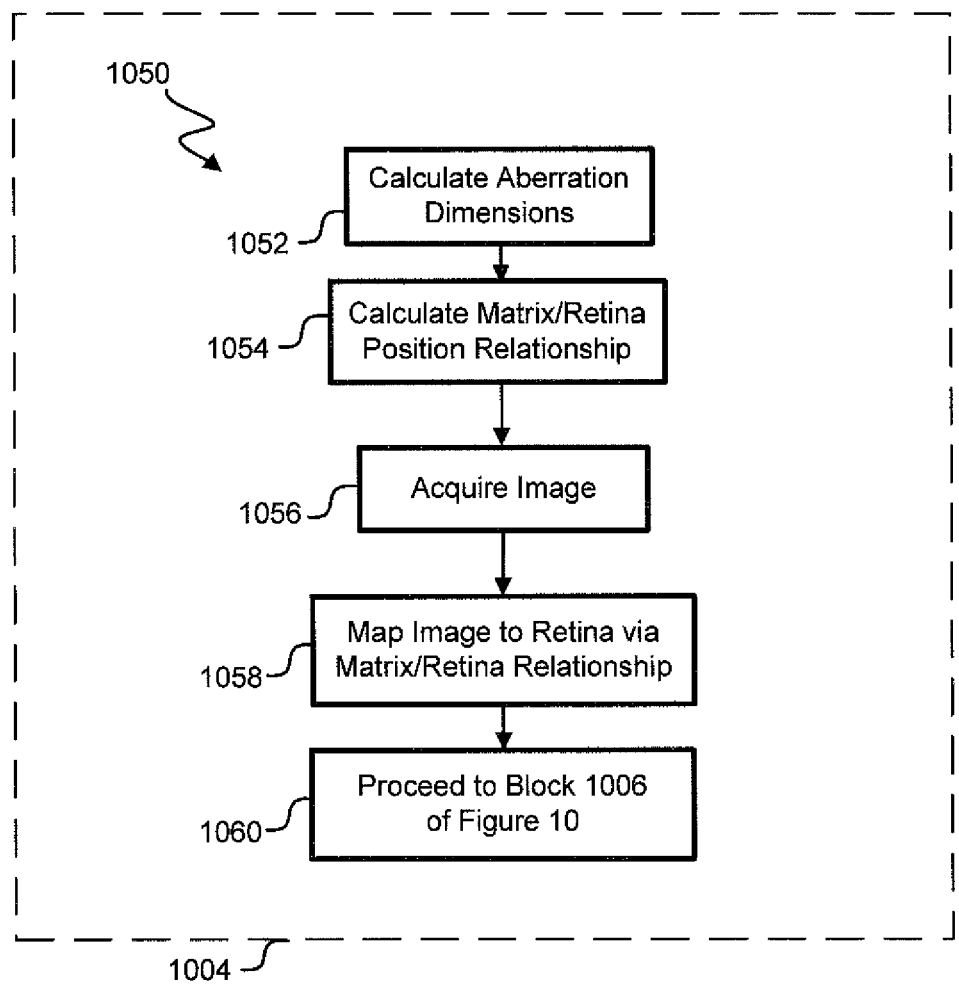
FIG. 10B is a flowchart illustrating one embodiment of a process for generating a custom wavefront.

With reference now to FIG. 10B, a flowchart illustrating a process 1050 for generating a custom wavefront is shown. In some embodiments, the process 1050 can be performed as a sub-process of block 1004 of FIG. 10. Process 1050 can be performed by the wavefront generator 112 and/or by one or several components of the wavefront generator 112 including, for example, the processor 130.

The process 1050 begins at block 1052 wherein aberration dimensions are calculated. In some embodiments, for example, this can include retrieving information stored in block 1030 of FIG. 10A. In some embodiments, this can include receiving an indication of an aberration in the user's eye 102 such as, for example, spherical power error, cylinder power error, spherical aberration the cornea, axial length, or any other refractive error requiring correction. This information can then be used to calculate Zernike coefficients describing the aberration.

After the aberration dimensions have been calculated, the process 1050 proceeds to block 1054 wherein the matrix/retina position relationship is calculated. In some embodiments, for example, in which the retina portion/sensor position relationship was stored in block 1030 of FIG. 10A, the process 1050 can proceed from block 1052 to block 1056. If this information was not stored in block 1030 of FIG. 10A, then the aberration dimensions calculated in block 1052 can be used to calculate the matrix/retina position relationship. In some embodiments, for example, Zernike coefficients can be used calculate, and thereby identify the correspondence between a position in the matrix of photoreceptors and/or sensors and/or a position in the matrix of individually controllable light sources and portions of the retina. This calculation can be performed by ray tracing in which a model of the eye is created based on retrieved biometric data about the eye, and the impingement of a ray on the matrix of photoreceptors and/or light sources is calculated for each point on the retina. In some embodiments in which the matrix is divided into subsets associated with a lenslet and/or mirror, this ray tracing can involve determining the position of the impingement of the central ray on the photoreceptors and/or light sources associated with each lenslet and/or mirror.

After the matrix/retina position relationship has been calculated, the process 1050 proceeds to block 1056 wherein the image data is acquired. In some embodiments, for example, this can include receiving image data with the communications engine 134. In some embodiments, for example, in which the wavefront generator 112 is associated with a camera, this can include receiving image data from the camera. In some embodiments, for example, the acquired image can comprise a complex image, including, for example, video images, and in some embodiments, this image can comprise a first image for imaging in the patient's and/or user's first eye and a second image for imaging in the patient's and/or user's second eye. Advantageously the imaging of the first image in the user's first eye and the imaging of the second image in the user's second eye can create a stereoscopic 3-D effect.

The image can comprise a variety of different data. In some embodiments, for example, the image can provide data relating to the user surrounding and can be, for example, generated by a camera associated with the wavefront generator 112. In some embodiments, for example, the image can provide data received from a data source such as, for example, an electronic device including a handheld electronic device such as a smart phone, tablet, a computer, and in some embodiments, the image can provide data relating to the user such as, for example, data relating to the users help including, for example, the user's blood pressure, heart rate, blood oxygenation level, blood sugar level, temperature, insulin level or cholesterol level.

In some embodiments, acquiring the image data can further comprise converting the image data to a format compatible with the wavefront generator 112. In some embodiments in which the wavefront generator 112 projects a matrix of dots onto the retina of the patient's eye, converting the image data to a format compatible with wavefront generator 112 can include the rasterization of the image data. In some embodiments, the rasterization of the image data can result in the creation of raster format image data which can be defined, for example, by a group of pixels and/or dots. In some embodiments, the wavefront generator can be configured to image these dots onto the retina, and in some embodiments, the way front generator 112 can be configured to independently image these dots onto the retina.

The size of the pixels and/or dots of the raster format image data can be varied to provide a desired resolution of the image on the retina. In some embodiments, the size of the pixels and/or dots the raster format image data can be based on the imaging capabilities of the wavefront generator 112.

After the image data has been acquired, the process 1050 proceeds to block 1058 wherein the image is mapped onto the retina via the matrix/retina relationship. In some embodiments, for example, this can include identifying portions of the matrix that can be used to create the image on the retina. This can include retrieving calculated matrix/retina position relationship and there with identifying portions of the matrix to operate to thereby create the image on the retina.

After the image has been mapped to the retina via the matrix/retina relationship, the process 1050 proceeds to block 1060 and proceeds to block 1006 of FIG. 10.

Figure 11:
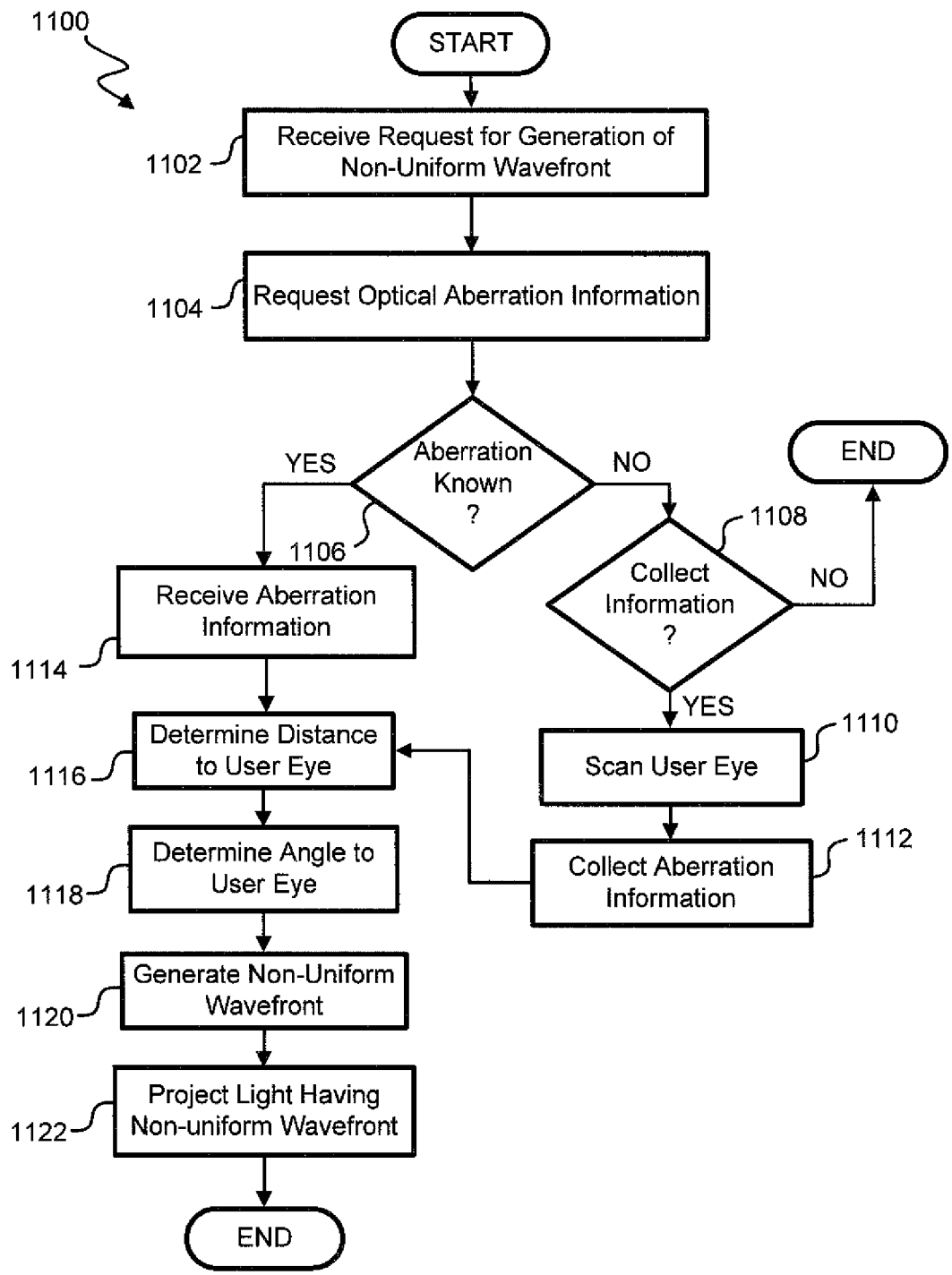
FIG. 11 is a flowchart illustrating a detailed embodiment of the process for projecting light having a custom wavefront.

With reference now to FIG. 11 a flowchart illustrating a detailed embodiment of a process 1100 for projecting light having a custom wavefront is shown. As discussed above, in some embodiments, this process 1000 can be used to generate light having a custom wavefront corresponding to the optical aberration of a user's eye. This correspondence between the custom wavefront and the optical aberration of the user's eye allows light having the custom wavefront to focus on the retina of the user's eye, and thereby allow the user to clearly see the projected light.

The process 1100 begins at block 1102 wherein a request for generation of a custom wavefront is received. In some embodiments, for example, in which custom wavefront generation is performed when requested by a user, the request for the generation of the custom wavefront can be received from the user via the input/output interface 132. In some embodiments, for example, in which custom wavefront generation is automatically performed when the user is detected, the request for the generation of the custom wavefront can be received from the processor 130 in response to the processor 130 receiving an indication of a user interaction with the wavefront generator 112. In some embodiments, for example, this indication of the user interaction can include detecting user interaction with the input/output interface 132 and/or detecting the presence of the user proximate to the wavefront generator 112 by, for example, scanning engine 138.

After the request for generation of the custom wavefront has been received, the process 1100 proceeds to block 1104 wherein optical aberration information is requested. In some embodiments, for example, the request for optical aberration information can be made by the processor 130 and/or other component of the wavefront generator 112 and can include providing a query to the user via the input/output interface 132 for known aberration information, providing a query to the user via the input output interface 132 for sources that possess and/or may possess aberration information including, for example, a medical service provider, querying an identified source for aberration information via the communication engine 134, and/or querying a portion of the memory 140 including, for example, the profile database 142 and/or the scanning database 144 for stored aberration information.

After the optical aberration information has been requested, the process 1100 proceeds to decision state 1106 wherein is determined if the aberration information is known. In some embodiments this determination can be made by the wavefront generator 112 and/or a component of the wavefront generator 112 including, for example, the processor. This determination can include the evaluation of data received in response to queries provided in block 1104.

If it is determined that aberration information is unknown, the process 1100 proceeds to decision state 1108 wherein it is determined if aberration information should be collected. In some embodiments, for example, the determination of whether aberration information should be collected can include determining whether aberration information can be collected by either the wavefront generator 112 for another source, and determining whether the user wants to have the aberration information collected. The aberration information should not be collected, then the process 1100 terminates.

If the aberration information should be collected, then the process 1100 proceeds to block 1110 wherein the user's eye is scanned. In some embodiments, for example, the user's eye can be scanned by the wavefront generator 112, and specifically by components of the wavefront generator such as, for example, the scanning engine 138. In some embodiments, for example, the user's eye can be scanned by a source such as a medical service provider.

After the user's eye has been scanned, the process 1100 proceeds to block 1112 wherein aberration information is collected. In some embodiments, for example, the collection of the aberration information can include the processing and/or analyzing of the data generated by the scan of the user's eye to convert the scanned data into aberration information.

Returning again to decision state 1106, if it is determined that aberration information is known, the process 1100 proceeds to block 1114 wherein the aberration information is received. In some embodiments, for example, the aberration information can be received by the wavefront generator 112 from the user, from the source, and/or from the memory 140. In some embodiments, for example, the aberration information can be received by components of the wavefront generator including, for example, the processor 130, the input output interface 132, and/or the communication engine 134.

After the aberration information has been received, or, returning to block 1112 after the aberration information has been collected, the process 1100 proceeds to block 1116 wherein the distance to the user eye is determined. In some embodiments, for example, the distance to the user eye can affect the custom wavefront that will, in combination with the optical aberration of the user's eye, focus projected light on the retina of the user's eye. The determination of the distance to the user's eye can be performed by a component of the scanning engine 138, including, for example, a sensor configured to determine the distance between the wavefront generator 112 and the user's eye.

After the distance of the user's eye has been determined, the process 1100 proceeds to block 1118 wherein the angle to the user's eye is determined. In some embodiments, for example, the angle of the wavefront generator 112 relative to the user's eye can affect the custom wavefront that in combination with the optical aberration of the user's eye, focuses projected light on the retina of the user's eye. The determination of the angle of the wavefront generator 112 relative to the user's eye can be performed by a component of the scanning engine 138 including, for example, a sensor configured to determine the angle between the wavefront generator 112 and the user's eye.

After the angle to the user's eye is determined, the process 1100 proceeds to block 1120 wherein the custom wavefront is generated. In some embodiments, the custom wavefront corresponds to optical aberration information, the distance to the user eye, and the angle to the user eye in that light having the custom wavefront and passing through the eye with that optical aberration and at the determined distance and angle focuses on the retina of the eye. In some embodiments, for example, the custom wavefront can be generated by a component of the wavefront generator 112 including, for example, the processor 130 and/or the projection engine 136. In some embodiments, for example, the custom wavefront can be retrieved from a component of the wavefront generator 112 including the input/output interface 132, the communication engine 134, and/or the memory 140 including the profile database 142 and/or the scanning database 144. In some embodiments, for example, the custom wavefront can be received input into the input/output interface 132 by the user and/or the custom wavefront can be received from another source including, for example, a computer configured to generate and/or store the custom wavefront via the communication engine 134.

In some embodiments, the steps depicted in blocks 1116 and 1118 can include using the scanning engine 138, and/or portions of the scanning engine 138 as a tracking system to determine the location of the central portion of the cornea and pupil and to detect the optical axis of the patient's and/or user's eye. In some embodiments, this information relating to the location of the central portion of the cornea and the pupil, and the optical axis of the patient's and/or users I can be used to optimize the custom wavefront.

After the custom waveform is generated, the process 1100 proceeds to block 1122 wherein light having the custom wavefront is projected. In some embodiments, for example, the projecting of light having the custom wavefront comprises manipulating the wavefront of the light so that the wavefront of the light matches the generated custom wavefront. In some embodiments, this can be performed by the projection engine 136 and/or a component of the projection engine 136 such as the wavefront display.

Figure 12:
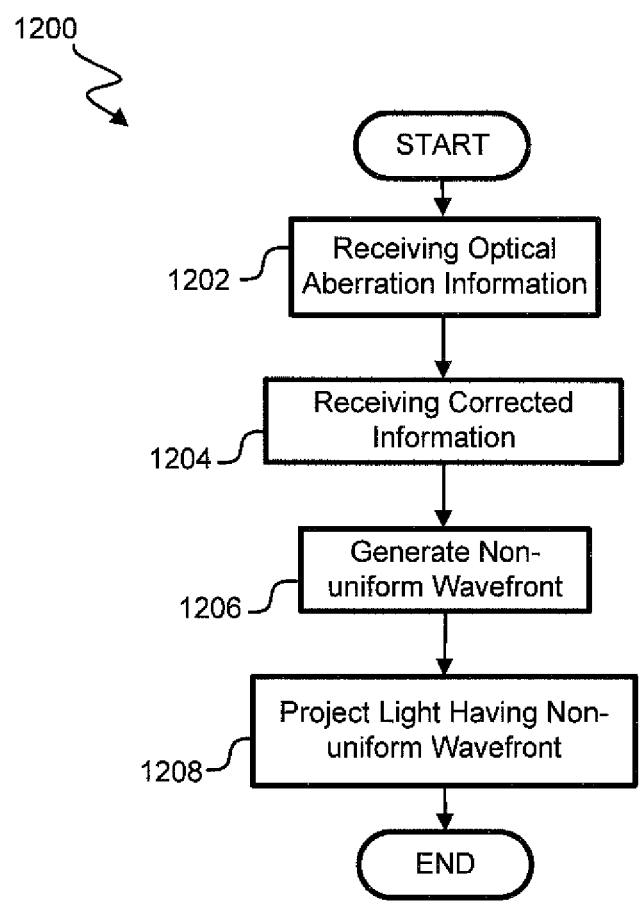
FIG. 12 is a flowchart illustrating one embodiment of a process for simulating a posttreatment condition.

With reference now to FIG. 12, a flowchart illustrating one embodiment of a process 1200 for simulating a post-treatment condition is shown. In some embodiments, for example, a treatment procedure can be recommended to a patient, which treatment procedure may result in the improvement of a condition. However, treatment procedures are frequently accompanied with costs and/or risks. As such, a patient and his doctor are required to determine whether to proceed with a treatment procedure in light of the costs and/or risks, but this decision can be complicated by the patient not understanding the desired and/or expected outcome of the treatment procedure. In light of this, the simulation of the posttreatment condition to allow the patient to experience the desired and/or expected results of the treatment procedure before undergoing the treatment procedure can be desirable.

The process 1200 can be performed by the wavefront generator 112, a component of the wavefront generator, and/or a system including the wavefront generator 112. The process begins at block 1202 wherein optical aberration information is received. In some embodiments, for example, the aberration information can be received by the wavefront generator 112 from the user, from the source, and/or from the memory 140. In some embodiments, for example, the aberration information can be received by components of the wavefront generator including, for example, the processor 130, the input output interface 132, and/or the communication engine 134.

After the optical aberration information has been received, the process 1200 proceeds to block 1204 wherein the corrected information is received. In some embodiments, for example, the corrected information can be data identifying the desired and/or expected optical characteristics including, for example, the refractive characteristics of the user's eye after the treatment procedure is performed. In some embodiments, for example, this information can be generated by component of the wavefront generator 112 including, for example, the processor 130. In some embodiments, for example, this information can be generated by a component and/or system other than the wavefront generator 112 such as, for example, a computer of a medical service provider, and can be provided to the wavefront generator 112 via the communication engine 134.

After the corrected information is received, the process 1200 proceeds to block 1206 wherein the custom wavefront is generated. In some embodiments, the custom wavefront corresponds to optical aberration information in that light having the custom wavefront and passing through the eye with that optical aberration focuses on the retina of the eye to the same extent that light having a uniform wavefront is expected and/or desired to focus on the retina of the eye after the treatment procedure. In some embodiments, for example, the custom wavefront can be generated by a component of the wavefront generator 112 including, for example, the processor 130 and/or the projection engine 136. In some embodiments, for example, the custom wavefront can be retrieved from a component of the wavefront generator 112 including the input/output interface 132, the communication engine 134, and/or the memory 140 including the profile database 142 and/or the scanning database 144. In some embodiments, for example, the custom wavefront can be received input into the input/output interface 132 by the user and/or the custom wavefront can be received from another source including, for example, a computer configured to generate and/or store the custom wavefront via the communication engine 134.

After the custom wavefront is generated, the process 1200 proceeds to block 1208 wherein light having the custom wavefront is projected. In some embodiments, for example, the projecting of light having the custom wavefront comprises manipulating the wavefront of the light so that the wavefront of the light matches the generated custom wavefront. In some embodiments, this can be performed by the projection engine 136 and/or a component of the projection engine 136 such as the wavefront display. In some embodiments, for example, this like can be projected onto the user's eye, and can focus on the retina of the user's eye.

Figure 13:
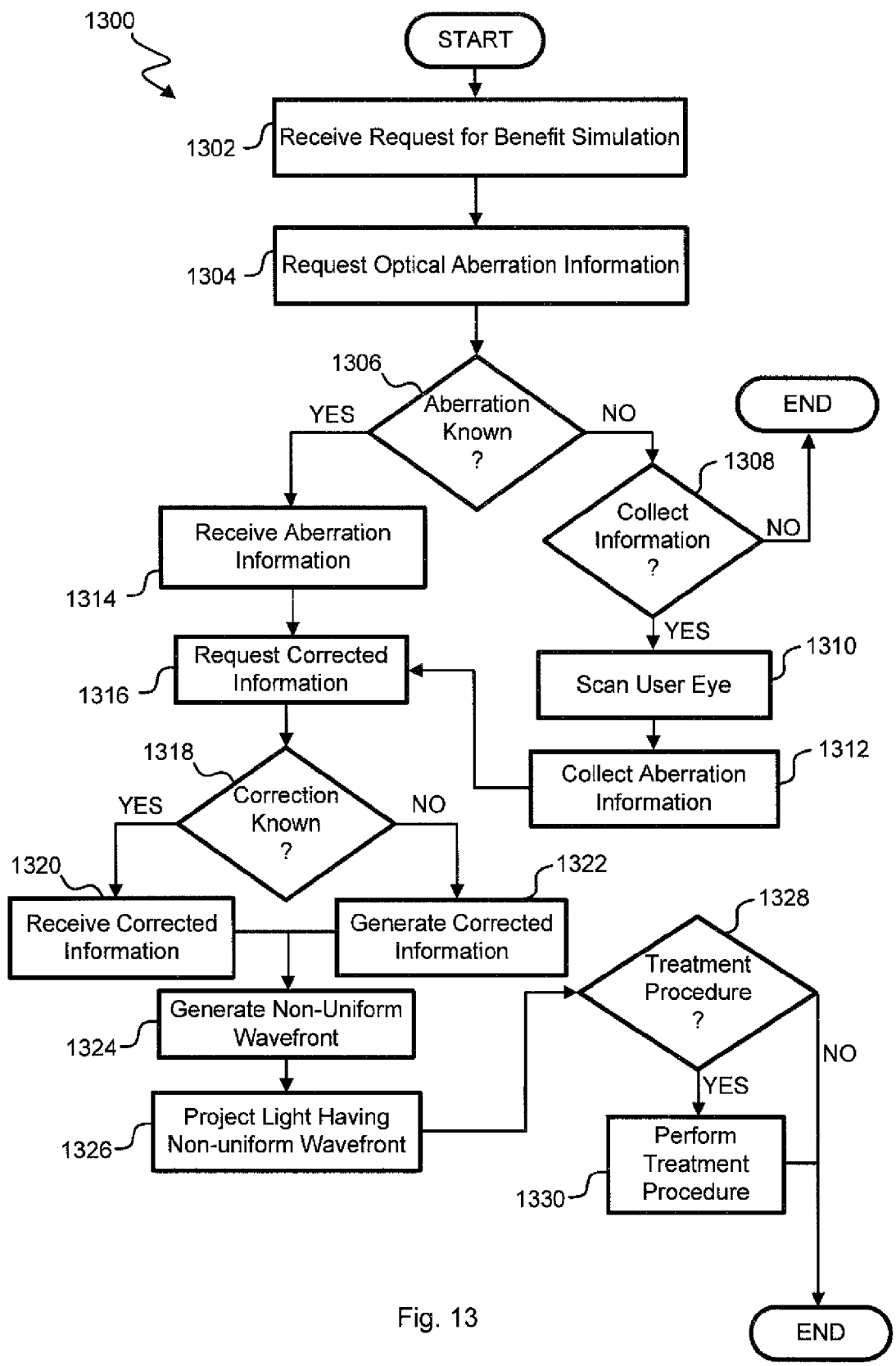
FIG. 13 is a flowchart illustrating a detailed embodiment of the process for simulating a posttreatment condition.

With reference now to FIG. 13, a flowchart illustrating a detailed embodiment of a process 1300 for simulating a posttreatment condition is shown. The process 1300 can be performed by the wavefront generator 112, component of the wavefront generator 112, and/or by a system including the wavefront generator 112. The process 1300 begins at block 1302 wherein the request for benefit simulation is received. In some embodiments, for example, the request for benefit simulation can be received from the user via the input/output interface 132.

After the request for benefit simulation has been received, the process 1300 proceeds to block 1304 wherein optical aberration information is requested. In some embodiments, for example, the request for optical aberration information can be made by the processor 130 and/or other component of the wavefront generator 112 or system including the wavefront generator 112 and can include providing a query to the user via the input/output interface 132 for known aberration information, providing a query to the user via the input output interface 132 for sources that possess and/or may possess aberration information including, for example, a medical service provider, querying and identified source for aberration information via the communication engine 134, and/or querying a portion of the memory 140 including, for example, the profile database 142 and/or the scanning database 144 for stored aberration information.

After the optical aberration information has been requested, the process 1300 proceeds to decision state 1306 wherein is determined if the aberration information is known. In some embodiments this determination can be made by the wavefront generator 112 and/or a component of the wavefront generator 112 including, for example, the processor. This determination can include the evaluation of data received in response to queries provided in block 1304.

If it is determined that aberration information is unknown, the process 1300 proceeds to decision state 1308 wherein it is determined if aberration information should be collected. In some embodiments, for example, the determination of whether aberration information should be collected can include determining whether aberration information can be collected by either the wavefront generator 112 or another source, and determining whether the user wants to have the aberration information collected. The aberration information should not be collected, then the process 1300 terminates.

If the aberration information should be collected, then the process 1300 proceeds to block 1310 wherein the user's eye is scanned. In some embodiments, for example, the user's eye can be scanned by the wavefront generator 112, and specifically by components of the wavefront generator such as, for example, the scanning engine 138. In some embodiments, for example, the user's eye can be scanned by a source such as a medical service provider.

After the user's eye has been scanned, the process 1300 proceeds to block 1312 wherein aberration information is collected. In some embodiments, for example, the collection of the aberration information can include the processing and/or analyzing of the data generated by the scan of the user's eye to convert the scanned data into aberration information.

Returning again to decision state 1306, if it is determined that aberration information is known, the process 1300 proceeds to block 1314 wherein the aberration information is received. In some embodiments, for example, the aberration information can be received by the wavefront generator 112 from the user, from the source, and/or from the memory 140. In some embodiments, for example, the aberration information can be received by components of the wavefront generator including, for example, the processor 130, the input output interface 132, and/or the communication engine 134.

After the aberration information has been received, or, returning to block 1312 after the aberration information has been collected, the process 1300 proceeds to block 1316 wherein the corrected information is requested. In some embodiments, for example, the corrected information can be data identifying the desired and/or expected optical characteristics including, for example, the refractive characteristics of the user's eye after the treatment procedure is performed. The request for the on can be made by the processor 130 and/or other component of the wavefront generator 112 or system including the wavefront generator 112 and can include providing a query to the user via the input/output interface 132 for known corrected information, providing a query to the user via the input output interface 132 for sources that possess and/or may possess corrected information including, for example, a medical service provider, querying and identified source for corrected information via the communication engine 134, and/or querying a portion of the memory 140 including, for example, the profile database 142 and/or the scanning database 144 for stored corrected information.

After the corrected information has been requested, the process 1300 proceeds to decision state 1318 wherein is determined if the corrected information is known. In some embodiments this determination can be made by the wavefront generator 112 and/or a component of the wavefront generator 112 including, for example, the processor. This determination can include the evaluation of data received in response to queries provided in block 1316.

If it is determined that the corrected information is known, the process 1300 proceeds to block 1320 wherein the corrected information is received. In some embodiments, the corrected information can be received from a component of the wavefront generator 112 and/or by a component the wavefront generator 112 such as, for example, the input/output interface 132 and/or the communication engine 134.

Returning again to decision state 1318, if the corrected information is not known, then the process 1300 proceeds to block 1322 wherein the corrected information is generated. In some embodiments, for example, the corrected information can be generated by component of the wavefront generator 112 including, for example, the processor 130. In some embodiments, for example, the corrected information can be generated by a component and/or system other than the wavefront generator 112 such as, for example, a computer of a medical service provider, and can be provided to the wavefront generator 112 via the communication engine 134.

After the corrected information is received, the process 1300 proceeds to block 1324 wherein the custom wavefront is generated. As discussed above, in some embodiments, the custom wavefront corresponds to optical aberration information in that light having the custom wavefront and passing through the eye with that optical aberration focuses on the retina of the eye to the same extent that light having a uniform wavefront is expected and/or desired to focus on the retina of the eye after the treatment procedure. The custom wavefront can be generated by a component of the wavefront generator 112 including, for example, the processor 130 and/or the projection engine 136. In some embodiments, the custom wavefront can be retrieved from a component of the wavefront generator 112 including the input/output interface 132, the communication engine 134, and/or the memory 140 including the profile database 142 and/or the scanning database 144, and in some embodiments the custom wavefront can be received input into the input/output interface 132 by the user and/or the custom wavefront can be received from another source including, for example, a computer configured to generate and/or store the custom wavefront via the communication engine 134.

After the custom wavefront is generated, the process 1300 proceeds to block 1326 wherein light having the custom wavefront is projected. In some embodiments, for example, the projecting of light having the custom wavefront comprises manipulating the wavefront of the light so that the wavefront of the light matches the generated custom wavefront. In some embodiments, this can be performed by the projection engine 136 and/or a component of the projection engine 136 such as the wavefront display. In some embodiments, for example, this like can be projected onto the user's eye, and can focus on the retina of the user's eye.

After the light having the custom wavefront is projected, the process 1300 moves to decision state 1328 wherein it is determined if the treatment procedure will be performed. In some embodiments, for example, the determination of whether the treatment procedure is to be performed can include providing a prompt and/or query to the user as to whether they want to proceed with the treatment procedure. In some embodiments, for example, this prompt can include information relating to the risk and/or cost associate with the treatment procedure as well as reference to the user experienced simulated outcome of the treatment procedure, and in some embodiments, information relating to the likelihood of achieving that experience simulated outcome. In some embodiments, the determination of whether the treatment procedure will be performed can further include receiving an input indicating whether to proceed with the treatment. In some embodiments, for example, this input can be received by the wavefront generator 112 come and specifically by, for example, the input/output interface 132 and/or the communication engine 134. If it is determined that the treatment procedure will not be performed, then the process 1300 terminates. If it is determined in decision state 1328 that the treatment procedure will be performed, then the process 1300 proceeds to block 1330 wherein the treatment procedure is performed.

Figure 14:
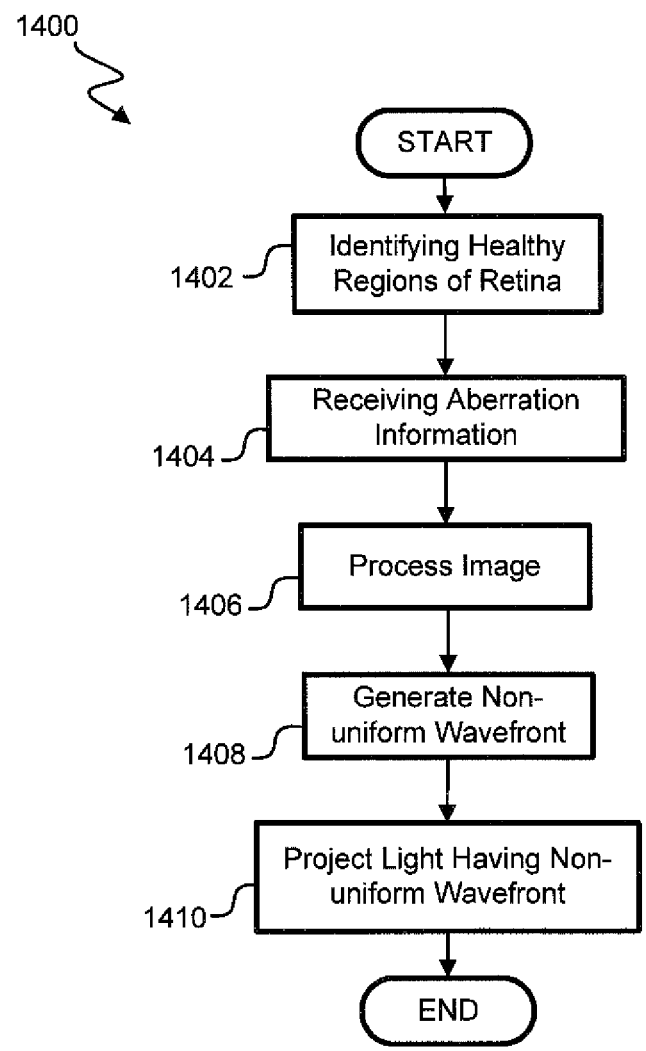
FIG. 14 is a flowchart illustrating one embodiment of a process for selective illumination of a retina.

With reference now to FIG. 14, a flowchart illustrating one embodiment of a process 1400 for selective illumination of the retina is shown. In some embodiments, for example, the function of portions of the retina can decay. This decay in the function of portions the retina can be caused, for example, by damage and/or injury to the retina, by disease, or by age. In some embodiments, the deterioration in the function portions of the retina can result in diminished vision ability including in blind spots.

The process 1400 begins at block 1402 wherein healthy regions of the retina are identified. In some embodiments, for example, this can include mapping the retina to identify the location of healthy regions of the retina, as well as unhealthy regions of the retina. This mapping can be performed by the wavefront generator 112 and/or a component of the wavefront generator 112 such as, for example, the projection engine 136 and/or the scanning engine 138.

After the healthy regions of the retina have been identified, the process 1400 proceeds to block 1404 wherein aberration information is received. In some embodiments, for example, the aberration information can be received by the wavefront generator 112 from the user, from the source, and/or from the memory 140. In some embodiments, for example, the aberration information can be received by components of the wavefront generator including, for example, the processor 130, the input output interface 132, and/or the communication engine 134.

After the aberration information has been received, the process 1400 proceeds to block 1406 wherein the image is processed. In some embodiments, for example, the image can comprise any image data that can be received by, for example, the wavefront generator 112 and/or a component of the wavefront generator. In some embodiments, for example, this image data can be generated by a camera associated with wavefront generator 112, which camera can be included in the scanning engine 138. In some embodiments, for example, the image processing can include the mapping of the image onto healthy portions of the retina so as to avoid projecting portions of the image onto the unhealthy retina portions. In some embodiments, this mapping of the image onto healthy portions of the retina can include distorting the image so as to allow the projection of the complete image onto the healthy portions of the retina.

After the image has been processed, the process 1400 proceeds to block 1408 wherein the custom waveform is generated. In some embodiments in which the image processing a block 1406 results in adjustments to the image data so as to allow the projection the complete image onto healthy portions of the retina, the generation of the custom wavefront can comprise generation of a custom wavefront configured to project the entire processed image onto healthy portions of the retina. As discussed above, in the context of FIGS. 10A and 10B, this can include identifying the matrix/retina relationship and determining which portions of the matrix to activate in order to project the processed image onto only healthy portions of the retina.

In some embodiments, the custom wavefront corresponds to optical aberration information in that light having the custom wavefront and passing through the eye having that optical aberration focuses on the retina of the eye. In some embodiments, for example, the custom wavefront can be generated by a component of the wavefront generator 112 including, for example, the processor 130 and/or the projection engine 136. In some embodiments, for example, the custom wavefront can be retrieved from a component of the wavefront generator 112 including the input/output interface 132, the communication engine 134, and/or the memory 140 including the profile database 142 and/or the scanning database 144. In some embodiments, for example, the custom wavefront can be input into the input/output interface 132 by the user and/or the custom wavefront can be received from another source including, for example, a computer configured to generate and/or store the custom wavefront via the communication engine 134.

After the custom waveform is generated, the process 1400 proceeds to block 1410 wherein light having the custom wavefront is projected onto the retina. In some embodiments, this can include projecting light corresponding to the processed image, and having the custom wavefront onto healthy portions of the retina. In some embodiments, for example, the projecting of light having the custom wavefront comprises manipulating the wavefront of the light so that the wavefront of the light matches the generated custom wavefront. In some embodiments, this can be performed by the projection engine 136 and/or a component of the projection engine 136 such as the wavefront display.

Figure 14A:
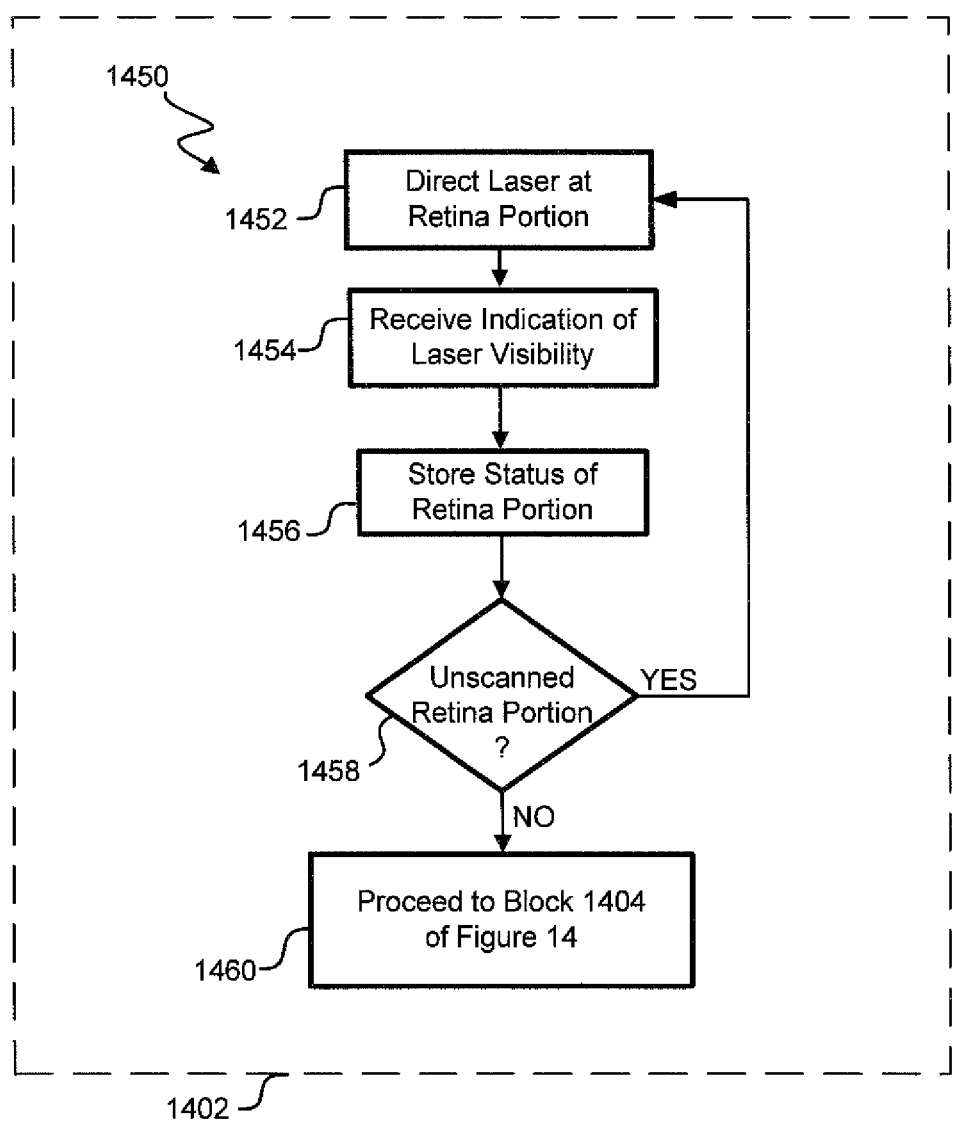
FIG. 14A is a flowchart illustrating one embodiment of a process for mapping a retina.

With reference now to FIG. 14A, a flowchart illustrating a process 1450 for mapping a retina is shown. In some embodiments, for example, this process 1450 can be performed as a sub process within in block 1402 of FIG. 14. This process 1450 can be performed by the wavefront generator 112 and/or a component of the wavefront generator 112 including, for example, the projection engine 136 and/or the scanning engine 138. Alternatively, this process 1450 can be performed by a component other than the wavefront generator 112, and information relating to the retina mapping can be provided to the wavefront generator 112 via, for example, the communication engine 134.

The process 1450 begins at block 1452 wherein a coherent beam of light is directed onto a portion of the retina. In some embodiments, the coherent beam of light can be configured so as not to temporarily and/or permanently damage the retina, but rather to reflect a portion of the coherent beam of light to allow the evaluation of the optical aberration of the eye. In some embodiments, for example, the coherent beam of light can comprise a laser.

After the coherent beam of light is directed onto a portion of the retina, the process 1450 proceeds to block 1454 wherein an indication of the visibility of the coherent beam of light is received. In some embodiments, for example, this indication can be provided by the user, and can be received by the wavefront generator 112 including a component of the wavefront generator 112 such as, for example, the input/output interface 132. In some embodiments, for example, this indication can be received by a person, system, and/or component other than the wavefront generator 112, and can be provided to the wavefront generator 112 via the communication engine 134.

After the indication of the visibility of the coherent beam of light has been received, the process 1450 proceeds to block 1456 wherein the status of the retina portion is stored. In some embodiments, for example, the status of the retina portion can be stored in, for example, the memory 140 of the wavefront generator 112 including, for example, in the profile database 142 and/or in the scanning database 144 of the memory 140. In some embodiments, for example, this retina status can include a binary Indicator of the health of that portion of the retina, wherein a first value indicating the health status of the retina portion can be assigned if the coherent beam of light is visible, and a second value indicating the unhealthy status of the retina portion can be assigned if the coherent beam of light is not visible.

After the status of the retina portion has been stored, the process 1450 proceeds to decision state 1458 wherein it is determined if the entire retina has been mapped. In some embodiments, for example, this can include determining whether there are portions of the retina that have not been scanned. If it is determined that there are portions the retina that have not been scanned, the process 1450 can return to block 1452 wherein a coherent beam of light is directed at a portion of the retina that has not been scanned. If it is determined that the entire retina has been mapped and/or that there are no remaining un-scanned retina portions, then the process 1450 can proceed to block 1460 and proceed to block 1404 of FIG. 14.

Figure 15:
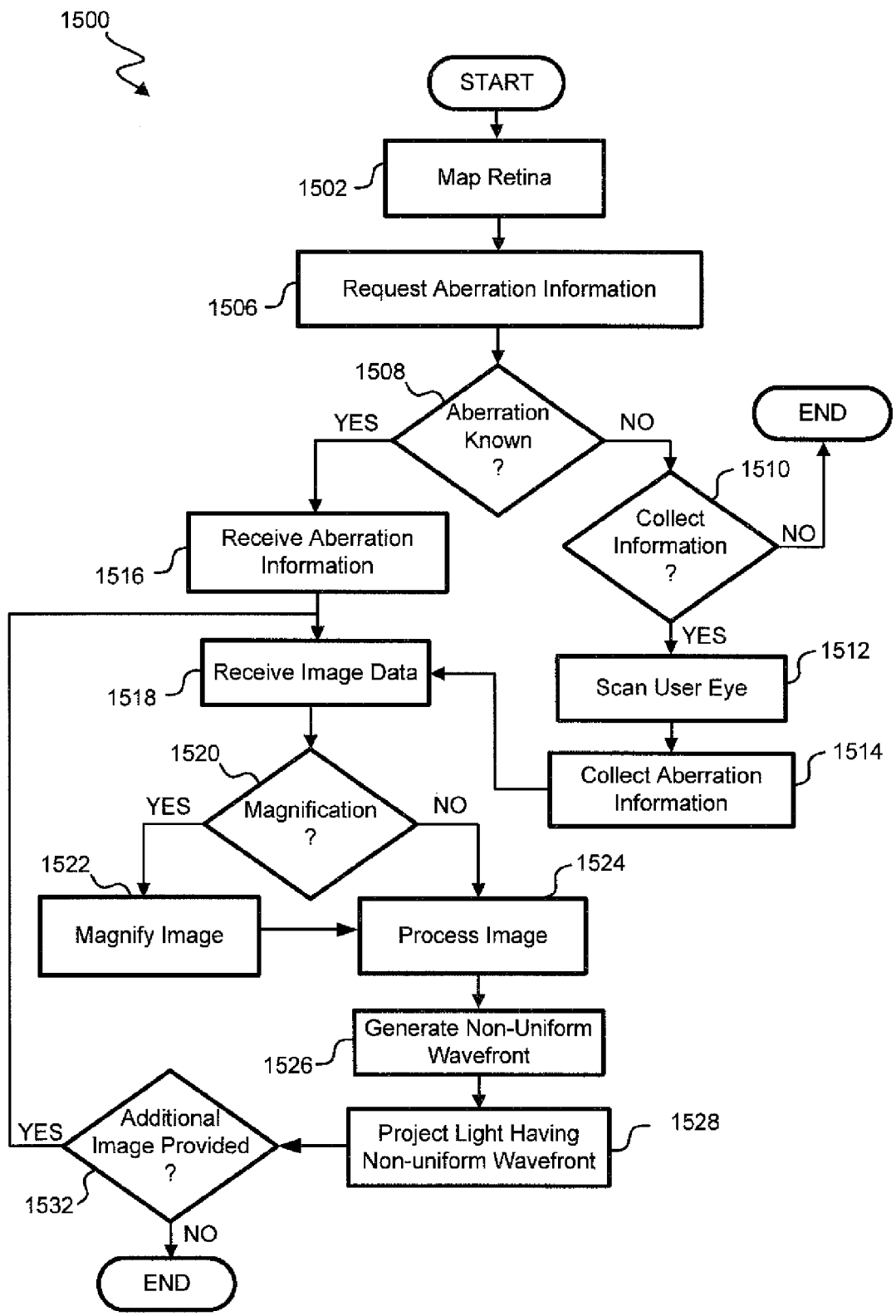
FIG. 15 is a flowchart illustrating a detailed embodiment of the process for selective illumination of a retina.

With reference to FIG. 15, flowchart illustrating a detailed embodiment of a process 1500 for selective illumination of the retina is shown. The process begins at block 1502 wherein the retina is mapped. In some embodiments, for example, the mapping of the retina can include the identification of healthy portions of the retina as well as the identification of unhealthy portions the retina. In some embodiments, for example, the mapping of the retina can be performed as outlined in FIG. 14A.

After the retina has been mapped, the process 1500 proceeds to block 1506 wherein optical aberration information is requested. In some embodiments, for example, the request for aberration information can be made by the processor 130 and/or other component of the wavefront generator 112 and can include providing a query to the user via the input/output interface 132 for known aberration information, providing a query to the user via the input output interface 132 for sources that possess and/or may possess aberration information including, for example, a medical service provider, querying and identified source for aberration information via the communication engine 134, and/or querying a portion of the memory 140 including, for example, the profile database 142 and/or the scanning database 144 for stored aberration information.

After the optical aberration information has been requested, the process 1500 proceeds to decision state 1508 wherein is determined if the aberration information is known. In some embodiments this determination can be made by the wavefront generator 112 and/or a component of the wavefront generator 112 including, for example, the processor. This determination can include the evaluation of data received in response to queries provided in block 1506.

If it is determined that aberration information is unknown, the process 1500 proceeds to decision state 1510 wherein it is determined if aberration information should be collected. In some embodiments, for example, the determination of whether aberration information should be collected can include determining whether aberration information can be collected by either the wavefront generator 112 from another source, and determining whether the user wants to have the aberration information collected. The aberration information should not be collected, then the process 1500 terminates.

If the aberration information should be collected, then the process 1500 proceeds to block 1512 wherein the user's eye is scanned. In some embodiments, for example, the user's eye can be scanned by the wavefront generator 112, and specifically by components of the wavefront generator such as, for example, the scanning engine 138. In some embodiments, for example, the user's eye can be scanned by a source such as a medical service provider.

After the user's eye has been scanned, the process 1500 proceeds to block 1514 wherein aberration information is collected. In some embodiments, for example, the collection of the aberration information can include the processing and/or analyzing of the data generated by the scan of the user's eye to convert the scanned data into aberration information.

Returning again to decision state 1508, if it is determined that aberration information is known, the process 1500 proceeds to block 1516 wherein the aberration information is received. In some embodiments, for example, the aberration information can be received by the wavefront generator 112 from the user, from the source, and/or from the memory 140. In some embodiments, for example, the aberration information can be received by components of the wavefront generator including, for example, the processor 130, the input output interface 132, and/or the communication engine 134.

After the aberration information has been received, or, returning to block 1514 after the aberration information has been collected, the process 1500 proceeds to block 1518 wherein the image data is received. In some embodiments, for example, this can include receiving and/or generating image data with the communications engine 134. In some embodiments, for example, in which the wavefront generator 112 is associated with a camera, this can include receiving image data from the camera.

After the image data has been received, the process 1500 proceeds to decision state 1520 wherein it is determined if the image data should be magnified. In some embodiments, for example, the wavefront generator 112 can include features configured to allow the user to select a magnification level. If the user has selected an elevated magnification level, or the wavefront generator 112 is set to provide an elevated magnification level, the process 1500 proceeds to block 1522 wherein the image is magnified. In some embodiments, for example, in which a camera is collecting the image data, the image can be optically magnified, and in some embodiments, the image can be digitally magnified.

After the image has been magnified, and returning again to decision state 1520 if it is determined that elevated magnification is not requested, then the process 1500 proceeds to block 1524 wherein the image is processed. The image processing can include the mapping of the image onto healthy portions of the retina so as to avoid projecting portions of the image onto the unhealthy retina portions. Specifically, in one embodiment, the image can be overlaid on a map of the retina, which overlay can be used to determine portions of the image that will be affected by unhealthy retina portions. In some embodiments, the portions of the image overlaying unhealthy retina portions, as well as the surrounding portions of the image overlaying healthy portions of the retina can be compressed so that no portion of the image is projected onto the unhealthy portions of the retina, but rather is projected onto the surrounding healthy portions of the retina. This image compression can result in distortions in the image projected around the unhealthy portions the retina. In some embodiments, the amount of image compression, and thereby also the amount of image distortion can be attenuated based on distance from the center of the unhealthy retina portion. Advantageously, the user can adjust to such image distortion and thereby be able to view an entire image.

After the image has been processed, the process 1500 proceeds to block 1526 wherein the custom wavefront is generated. In some embodiments in which the image processing a block 1524 results in adjustments to the image data so as to allow the projection the complete image onto healthy portions of the retina, the generation of the custom wavefront can comprise generation of a custom wavefront configured to project the entire processed image onto healthy portions of the retina. As discussed above, in the context of FIGS. 10A and 10B, this can include identifying the matrix/retina relationship and determining which portions the matrix to activate in order to project the process image onto only healthy portions of the retina.

In some embodiments, the custom wavefront corresponds to optical aberration information in that light having the custom wavefront and passing through the eye having that optical aberration focuses on the retina of the eye. In some embodiments, for example, the custom wavefront can be generated by a component of the wavefront generator 112 including, for example, the processor 130 and/or the projection engine 136. In some embodiments, for example, the custom wavefront can be retrieved from a component of the wavefront generator 112 including the input/output interface 132, the communication engine 134, and/or the memory 140 including the profile database 142 and/or the scanning database 144. In some embodiments, for example, the custom wavefront can be received input into the input/output interface 132 by the user and/or the custom wavefront can be received from another source including, for example, a computer configured to generate and/or store the custom wavefront via the communication engine 134.

After the custom waveform is generated, the process 1500 proceeds to block 1528 wherein light having the custom wavefront is projected onto the retina. In some embodiments, this can include projecting light corresponding to the processed image, and having the custom wavefront onto healthy portions of the retina. In some embodiments, for example, the projecting of light having the custom wavefront comprises manipulating the wavefront of the light so that the wavefront of the light matches the generated custom wavefront. In some embodiments, this can be performed by the projection engine 136.

In some embodiments, the wavefront generator 112 can be configured to identify features on the retina so as to allow the proper placement, alignment, and/or orientation of the projected image onto the retina. In some embodiments, for example, a feature of the scanning engine 138 such as, for example, a camera and/or an infrared camera can be used to identify reference features of the eye such as, for example, the pupil center and/or features of the retina, such as the location of veins that can be used as reference veins.

After light having the custom wavefront is projected onto the retina, the process 1500 proceeds to decision state 1532 wherein it is determined if additional image information is provided. In some embodiments, for example, the wavefront generator 112 may be configured to provide multiple images, continuous images, and/or streaming images to the user. In such an embodiment, the wavefront data may receive image data in addition to that which has been projected. If additional image data is provided, then the process 1500 returns to block 1518. If no additional image data it is provided, then the process terminates.

Figure 16:
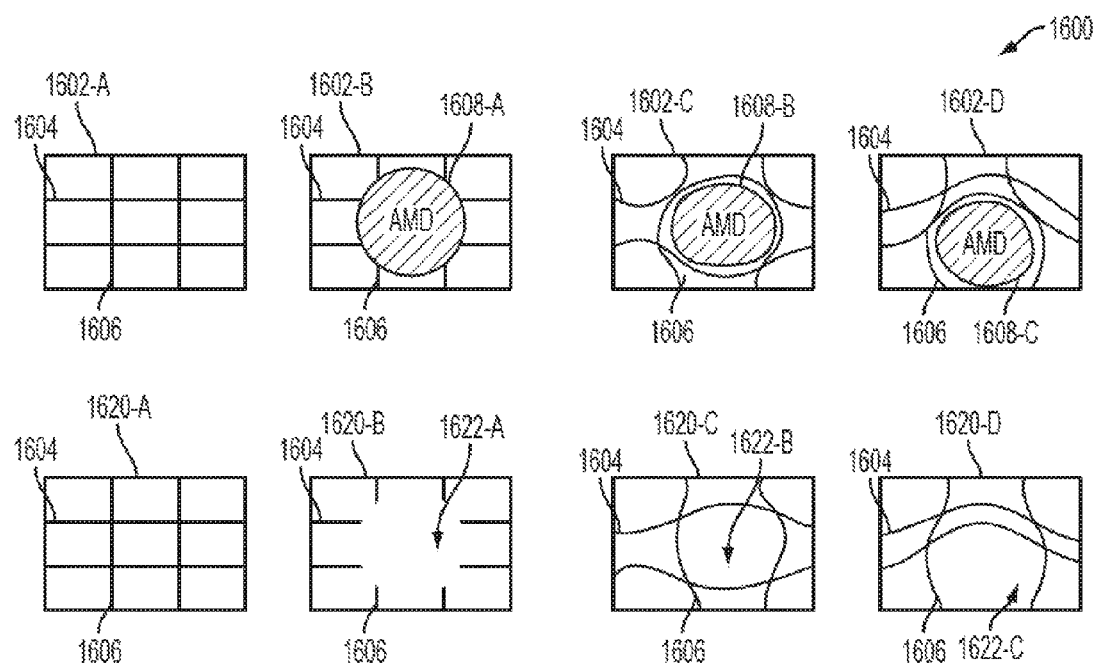
FIG. 16 is a schematic illustration of retinal condition and seen image resulting from the retinal condition.

With reference now to FIG. 16, a schematic illustration 1600 and of retinal condition and seen image resulting from the retinal condition is shown. FIG. 16 depicts a series of retina images 1602. These retina images 1602 represent the status of a retina and/or a portion of the retina, thus healthy retina image 1602-A represents the status of a healthy retina and first unhealthy retina image 1602-B, second unhealthy retina image 1602-C and third unhealthy retina image 1602-D represent the status of an unhealthy retina.

Each of the retina images includes horizontal image lines 1604 and vertical image lines 1606. These lines represent an image projected onto the retina.

The unhealthy retina images 1602-B, 1602-C, 1602-D further include an unhealthy retina portion 1608. The first unhealthy retina image 1602-B includes the first unhealthy retina portion 1608-A, the second unhealthy retina image 1602-C includes the second unhealthy retina portion 1608-B, and the third unhealthy retina image 1602-D includes the third unhealthy retina portion 1608-C. In some embodiments, for example, this unhealthy retina portion can correspond to a portion of the retina affected by macular degeneration including, for example, age-related macular degeneration.

FIG. 16 further depicts a series of seen images 1620. These seen images 1620 show what a user having a corresponding retina condition perceives as the image. Thus, the first seen image 1620-A corresponds to the healthy retina image 1602-A, the second seen image 1620-B corresponds to the first unhealthy retina image 1602-B, the third seen image 1620-C corresponds to the second unhealthy retina image 1602-C, and the fourth seen image 1620-D corresponds to the third unhealthy retina image 1602-D. Like the retina images 1602, the seen images 1620 include horizontal image lines 1604 and vertical image lines 1606, which lines represent the image projected onto the retina.

As depicted in the first and second seen images 1620-A, 1620-B, while the individual having the healthy retina perceives the entire image, as seen image 1620-A, the individual having the unhealthy retina portion does not see the affected image portion 1622-A.

In contrast to the second seen image 1620-B, the third and fourth seen images 1620-C, 1620-D depict the image perceived by a user having an unhealthy retina portion when the user's retina is illuminated in accordance with the steps described in FIGS. 14 through 15 above. As seen in the second and third unhealthy retina images 1602-C, 1602-D, the image as depicted by the horizontal and vertical image lines 1604, 1606 is distorted so as to be projected around the unhealthy retina portion 1608-B, 1608-C. Thus, no portion of the image is projected onto the unhealthy retina portion 1608-B, 1608-C. Due to the adaptive capability of the brain, this image distortion results in a perceived complete, albeit distorted image. Thus, in contrast to the second seen image 1620-B having an affected image portion 1622-A in which the affected image portion is missing, third and fourth seen images 1620-C, 1620-D have affected image portion 1622-B, 1622-C in which the affected image portion is merely distorted. Thus, by using the above outline techniques, the user perceives the complete, albeit distorted image.

A number of variations and modifications of the disclosed embodiments can also be used. Specific details are given in the above description to provide a thorough understanding of the embodiments. However, it is understood that the embodiments may be practiced without these specific details. For example, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perforin the functions described above, and/or a combination thereof.

Also, it is noted that the embodiments may be described as a process which is depicted as a flowchart, a flow diagram, a swim diagram, a data flow diagram, a structure diagram, or a block diagram. Although a depiction may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the tem "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A method of projecting a desired image, the method comprising:
   receiving data identifying an optical aberration in a user's eye;
   calculating a custom wavefront based on the data identifying the optical aberration in the user's eye;
   calculating a modified version of the image using the desired image and the custom wavefront, wherein the desired image has a plurality of image elements and the modified version of the image has a corresponding plurality of image elements;
   displaying the modified image on a display device; and
   projecting the modified image from the display device, through a lenslet array, and toward the eye to form a projected image on a retina of the eye, the projected image having a plurality of image elements corresponding to the plurality of image elements of the modified image, wherein the calculated modification of the image compensates for the custom wavefront so that the optical aberration of the user's eye alters the projected image from the modified image toward the desired image.

2. The method of claim 1, further comprising measuring the optical aberration in the user's eye.

3. The method of claim 2, wherein the optical aberration in the user's eye is measured with a Shack-Hartmann analyzer.

4. The method of claim 1, wherein the custom wavefront in combination with the optical aberration of the user's eye causes the projection of the image to focus on the retina of the user's eye.

5. The method of claim 4, wherein the projection of the image focuses on the retina of the user's eye when the display device is a specified distance and angle from the user's eye.

6. The method of claim 5 further comprising:
measuring the distance between the user's eye and the display device; and
adjusting the custom wavefront so that the specified distance between the user's eye and the display device is the measured distance between the user's eye and the display device.

7. The method of claim 6 further comprising:
measuring the angle between the user's eye and the display device; and
adjusting the custom wavefront so that the specified angle between the user's eye and the display device is the measured angle between the user's eye and the display device.

8. The method of claim 1, further comprising receiving image data for projection.

9. The method of claim 8, wherein the image data is generated by a user controlled camera.

10. The method of claim 9, wherein the image data comprises at least one of a landscape and a text string.

11. A method of simulating benefits of a vision correction, the method comprising:
generating optical aberration data for an eye of a patient;
generating a custom wavefront solution, wherein the custom wavefront solution represents a custom wavefront which in combination with the optical aberration of the patient's eye causes light to focus on the retina of the patient's eye to the same extent as light is expected to focus on the patient's retina after performing a corrective eye procedure;
calculating a modified version of an image using a desired image and the custom wavefront, wherein the desired image has a plurality of image elements and the modified version of the image has a corresponding plurality of image elements;
displaying the modified image on a display device;
projecting the modified image from the display device, through a lenslet array, and toward the eye to form a projected image on a retina of the eye, the projected image having a plurality of image elements corresponding to the plurality of image elements of the modified image, wherein the calculated modification of the image compensates for the custom wavefront so that the optical aberration of the user's eye alters the projected image from the modified image toward the desired image and thereby simulates corrected eyesight; and
performing the corrective procedure on the patient's eye.

12. The method of claim 11, wherein the light is projected onto the patient's eye with a Shack-Hartmann projector.

13. The method of claim 11, wherein the custom wavefront corrects for at least one of: myopia, hyperopia, and astigmatism.

14. A method of limiting the effects of macular degeneration, the method comprising:
determining the location of unhealthy regions of the retina of a patient's eye;
determining the location of healthy regions of the retina of the patient's eye;
generating optical aberration data for the patient's eye;
generating a custom wavefront solution, wherein the custom wavefront solution represents a custom wavefront which in combination with the optical aberration of the patient's eye causes an image to focus on the retina of the patient's eye;
calculating a modified version of an image using a desired image and the custom wavefront solution;
calculating a deformed version of the modified version of the image, wherein the deformations correspond to the location of the healthy and unhealthy regions of the patient's eye such that the image is projectable onto only the healthy portions of the retina, wherein the desired image has a plurality of image elements and each of the modified version of the image and the deformed image has a corresponding plurality of image elements; and
projecting the deformed version of the image from a display device, through a lenslet array, and toward the healthy portions of the retina to form a projected image on the retina.

15. The method of claim 14, wherein the unhealthy portions of the retina of the patient's eye comprise portions of the retina affected by macular degeneration.

16. The method of claim 15, wherein the macular degeneration is age related macular degeneration.

17. The method of claim 14, further comprising determining the orientation of the patient's eye relative to the display device.

18. The method of claim 17, wherein determining the orientation of the patient's eye comprises scanning the patient's eye and identifying a reference feature of the eye.

19. The method of claim 17, further comprising orienting the projected deformed image relative to the patient's eye so that the image is projected onto only the healthy regions of the retina.

20. The method of claim 14, further comprising receiving an indicator of a magnification level.

21. The method of claim 20, further comprising magnifying the image according to the received indicator of a magnification level.

* * * * *